(12) United States Patent
Kubota et al.

(10) Patent No.: US 11,366,339 B2
(45) Date of Patent: Jun. 21, 2022

(54) STICK ON DEVICES USING PERIPHERAL DEFOCUS TO TREAT PROGRESSIVE REFRACTIVE ERROR

(71) Applicant: ACUCELA INC., Seattle, WA (US)

(72) Inventors: Ryo Kubota, Seattle, WA (US); Philip M. Buscemi, Mount Pleasant, SC (US); Amitava Gupta, Roanoke, VA (US); Stefan Bauer, Bern (CH); Benjamin Crook, Bern (CH); Julien Sauvet, Biel (CH)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/304,630

(22) Filed: Jun. 23, 2021

(65) Prior Publication Data

US 2021/0382326 A1    Dec. 9, 2021

Related U.S. Application Data

(63) Continuation of application No. PCT/US2021/036102, filed on Jun. 7, 2021.
(Continued)

(51) Int. Cl.
*G02C 7/08* (2006.01)
*G02C 7/06* (2006.01)
(Continued)

(52) U.S. Cl.
CPC ............... *G02C 7/08* (2013.01); *G02C 7/022* (2013.01); *G02C 7/06* (2013.01); *G02C 7/10* (2013.01); *G02C 7/14* (2013.01); *G02C 2202/24* (2013.01)

(58) Field of Classification Search
CPC .......... G02C 7/08; G02C 7/088; G02C 7/022; G02C 7/027; G02C 7/04; G02C 7/042;
(Continued)

(56) References Cited

U.S. PATENT DOCUMENTS

| 6,516,808 B2 | 2/2003 | Schulman |
| 7,018,040 B2 | 3/2006 | Blum |
(Continued)

FOREIGN PATENT DOCUMENTS

| EP | 3413116 | 12/2018 |
| KR | 20180038359 | 4/2018 |
(Continued)

OTHER PUBLICATIONS

U.S. Appl. No. 17/303,889, filed Jun. 9, 2021 (69 pages).
(Continued)

*Primary Examiner* — Mustak Choudhury
(74) *Attorney, Agent, or Firm* — Fisherbroyles LLP; John Shimmick

(57) ABSTRACT

An apparatus to treat refractive error of an eye comprises an optic comprising an optical zone and a peripheral defocus optical structure to form images of a plurality of stimuli anterior or posterior to a peripheral portion of a retina of the eye. In some embodiments, the peripheral defocus optical structure located outside the optical zone. In some embodiments, the peripheral defocus optical structure comprises optical power to focus light to a different depth of the eye than the optical zone. In some embodiments, the optic comprises one or more of a lens, an optically transparent substrate, a beam splitter, a prism, or an optically transmissive support.

18 Claims, 19 Drawing Sheets

Related U.S. Application Data

(60) Provisional application No. 63/036,234, filed on Jun. 8, 2020.

(51) Int. Cl.
    *G02C 7/14*     (2006.01)
    *G02C 7/10*     (2006.01)
    *G02C 7/02*     (2006.01)

(58) Field of Classification Search
    CPC ........ G02C 7/044; G02C 7/045; G02C 7/047; G02C 7/049; G02C 7/06; G02C 7/10; G02C 7/14; G02C 11/10; G02C 2202/12; G02C 2202/20; G02C 2202/22; G02C 2202/24
    See application file for complete search history.

(56) References Cited

U.S. PATENT DOCUMENTS

| | | |
|---|---|---|
| 8,246,167 B2 | 8/2012 | Legerton |
| 8,432,124 B2 | 4/2013 | Foster |
| 8,662,664 B2 | 3/2014 | Artal Soriano |
| 8,857,983 B2 | 10/2014 | Pugh |
| 9,345,813 B2 | 5/2016 | Hogg |
| 9,763,827 B2 | 9/2017 | Kelleher |
| 9,885,884 B2 | 2/2018 | Drobe |
| 9,918,894 B2 | 3/2018 | Lam |
| 10,133,092 B2 | 11/2018 | Tsubota |
| 10,146,067 B2 | 12/2018 | Tsai |
| 10,231,897 B2 | 3/2019 | Tse |
| 10,268,050 B2 | 4/2019 | To |
| 10,788,686 B2 | 9/2020 | Tsai |
| 10,884,264 B2 | 1/2021 | Hones |
| 10,921,612 B2 | 2/2021 | Zhou |
| 10,993,515 B1 | 5/2021 | Kim |
| 11,000,186 B2 | 5/2021 | Linder |
| 11,187,921 B2 | 11/2021 | Zhou |
| 2002/0186345 A1 | 12/2002 | Duppstadt |
| 2004/0237971 A1 | 12/2004 | Radhakrishnan |
| 2006/0082729 A1 | 4/2006 | To |
| 2007/0115431 A1* | 5/2007 | Smith, III .............. G02C 7/042 351/221 |
| 2008/0291391 A1 | 11/2008 | Meyers |
| 2008/0309882 A1 | 12/2008 | Thorn |
| 2009/0187242 A1 | 7/2009 | Weeber |
| 2009/0204207 A1 | 8/2009 | Blum |
| 2010/0076417 A1 | 3/2010 | Suckewer |
| 2010/0296058 A1 | 11/2010 | Ho |
| 2011/0085129 A1 | 4/2011 | Legerton |
| 2011/0153012 A1 | 6/2011 | Legerton |
| 2011/0202114 A1 | 8/2011 | Kessel |
| 2012/0199995 A1 | 8/2012 | Pugh |
| 2012/0206485 A1 | 8/2012 | Osterhout |
| 2012/0212399 A1 | 8/2012 | Border |
| 2012/0215291 A1 | 8/2012 | Pugh |
| 2013/0027655 A1 | 1/2013 | Blum |
| 2013/0278887 A1 | 10/2013 | Legerton |
| 2014/0039361 A1 | 2/2014 | Siu |
| 2014/0194773 A1 | 7/2014 | Pletcher |
| 2014/0218647 A1 | 8/2014 | Blum |
| 2014/0240665 A1 | 8/2014 | Pugh |
| 2014/0268029 A1 | 9/2014 | Pugh |
| 2014/0277291 A1 | 9/2014 | Pugh |
| 2015/0057701 A1 | 2/2015 | Kelleher |
| 2015/0109574 A1 | 4/2015 | Tse |
| 2015/0160477 A1 | 6/2015 | Dai |
| 2015/0241706 A1 | 8/2015 | Schowengerdt |
| 2016/0056498 A1 | 2/2016 | Flitsch |
| 2016/0067037 A1* | 3/2016 | Rosen .................. A61F 2/1645 623/6.23 |
| 2016/0091737 A1 | 3/2016 | Kim |
| 2016/0143801 A1 | 5/2016 | Lam |
| 2016/0158486 A1 | 6/2016 | Colbaugh |
| 2016/0270656 A1 | 9/2016 | Samec |
| 2016/0377884 A1* | 12/2016 | Lau .................. G02C 7/022 351/159.05 |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0184875 A1 | 6/2017 | Newman |
| 2017/0270636 A1 | 9/2017 | Shtukater |
| 2017/0276963 A1 | 9/2017 | Brennan |
| 2017/0307779 A1 | 10/2017 | Marullo |
| 2018/0017810 A1 | 1/2018 | Wu |
| 2018/0017814 A1 | 1/2018 | Tuan |
| 2018/0052319 A1 | 2/2018 | McCabe |
| 2018/0055351 A1 | 3/2018 | Yates |
| 2018/0074322 A1 | 3/2018 | Rousseau |
| 2018/0090958 A1 | 3/2018 | Steger |
| 2018/0092738 A1 | 4/2018 | Tai |
| 2018/0136486 A1 | 5/2018 | MacNamara |
| 2018/0161231 A1 | 6/2018 | Tse |
| 2018/0173010 A1 | 6/2018 | Harant |
| 2018/0188556 A1 | 7/2018 | Portney |
| 2018/0221140 A1 | 8/2018 | Rosen |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1 | 1/2019 | Neitz |
| 2019/0049730 A1 | 2/2019 | Miller |
| 2019/0076241 A1 | 3/2019 | Alarcon Heredia |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250432 A1 | 8/2019 | Kim |
| 2019/0314147 A1 | 10/2019 | Blum |
| 2020/0033637 A1 | 1/2020 | Jamshidi |
| 2020/0089023 A1 | 3/2020 | Zhou |
| 2020/0110265 A1 | 4/2020 | Serdarevic |
| 2020/0133024 A1 | 4/2020 | Paune Fabre |
| 2020/0142219 A1 | 5/2020 | Rousseau |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0263336 A1 | 8/2021 | Gupta |
| 2021/0298440 A1 | 9/2021 | Kim |
| 2021/0356767 A1 | 11/2021 | Kubota |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |

FOREIGN PATENT DOCUMENTS

| | | |
|---|---|---|
| KR | 20180038359 A | 4/2018 |
| WO | 2009074638 | 6/2009 |
| WO | 2009074638 A3 | 6/2009 |
| WO | 2009121810 | 10/2009 |
| WO | 2010043599 | 4/2010 |
| WO | 2011089042 | 7/2011 |
| WO | 2012136470 | 10/2012 |
| WO | 2013087518 | 6/2013 |
| WO | 2014033035 | 3/2014 |
| WO | 2014191460 | 12/2014 |
| WO | 2015063097 | 5/2015 |
| WO | 2015186723 | 12/2015 |
| WO | 2018014712 | 1/2018 |
| WO | 2018014960 | 1/2018 |
| WO | 2018085576 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |

(56) References Cited

FOREIGN PATENT DOCUMENTS

| WO | 2021056018 | 3/2021 |
|----|------------|--------|
| WO | 2021168481 | 8/2021 |
| WO | 2021231684 | 11/2021 |
| WO | 2021252318 | 12/2021 |
| WO | 2021252319 | 12/2021 |
| WO | 2021252320 | 12/2021 |

OTHER PUBLICATIONS

U.S. Appl. No. 17/304,691, filed Jun. 24, 2021 (88 pages).
Wallman, Josh, et al., "Homeostasis of Eye Growth and the Question of Myopia," Neuron, 43:447-468 (2004).
Wolffsohn, James A., et al., "Impact of Soft Contact Lens Edge Design and Midperipheral Lens Shape on the Epithelium and Its Indentation With Lens Mobility," IOVS, 54(9):6190-6196 (2013).
Adler, Daniel, et al., "The possible effect of under correction on myopic progression in children," Clin Exp Optom., 89:315-321 (2006).
Aleman, Andrea C., et al.,, "Reading and Myopia: Contrast Polarity Matters," Scientific Reports, 8 pages (2018).
Arden, G.B., et al., "Does dark adaptation exacerbate diabetic retinopathy? Evidence and a linking hypothesis," Vision Research 38:1723-1729 (1998).
Arden, GB, et al, "Regression of early diabetic macular edema is associated with prevention of dark adaptation", in Eye, (2011). 25, pp. 1546-1554.
Benavente-Perez, A., et al., "Axial Eye Growth and Refractive Error Development Can Be Modified by Exposing the Peripheral Retina to Relative Myopic or Hyperopic Defocus," Invest Ophthalmol Vis Sci., 55:6765-6773 (2014).
Bonar, JR, et al, "High brightness low power consumption microLED arrays", in SPIE DigitalLibrary.org/conference-proceedings-of-spie, SPIE OPTO, 2016, San Francisco, California, United States, Abstract Only.
Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).
Chakraborty, R., et al., "Diurnal Variations in Axial Length, Choroidal Thickness, Intraocular Pressure, and Ocular Biometrics," IOVS, 52(8):5121-5129 (2011).
Chakraborty, R., et al., "Hyperopic Defocus and Diurnal Changes in Human Choroid and Axial Length," Optometry and Visual Science, 90(11):1187-1198 (2013).
Chakraborty, R., et al, "Monocular Myopic Defocus and Daily Changes in Axial Length and Choroidal Thickness of human Eyes," Exp Eye Res, 103:47-54 (2012).
Cooper, J., et al, "Current status of the development and treatment of myopia", Optometry, 83:179-199 (2012).
Cooper, J., et al., "A Review of Current Concepts of the Etiology and Treatment of Myopia," Eye & Contact Lens, 44(4):231-247 (Jul. 2018).
Demory, B., et al, "Integrated parabolic microlenses on micro LED color pixels", in Nanotechnology, (2018); 29, 16, pp. 1018, Abstract Only.
Dolgin, Elie, "The Myopia Boom," Nature 519:276-278 (2015).
Edrington, Timothy B., "A literature review: The impact of rotational stabilization methods on toric soft contact lens performance," Contact Lens & Anterior Eye, 34:104-110 (2011).
Flitcroft, D.I., "The complex interactions of retinal, optical and environmental factors in myopia aetiology," 31(6):622-660 (2012).
Garner, L.F., et al., "Crystalline Lens Power in Myopia," Optometry and Vision Science, 69:863-865 (1992).
Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).
Gwiazda, Jane, et al, "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).
Haglund, Erik, et al., "Multi-wavelength VCSEL arrays using high-contrast gratings," Proc. of SPIE vol. 10113, 7 pages (2017).
Hammond, D.S., et al, "Dynamics of active emmetropisation in young chicks—influence of sign and magnitude of imposed defocus" Ophthalmic Physiol Opt. 33:215-222 (2013).
Henry W., "MicroLED Sources enable diverse ultra-low power applications", in Photonic Spectra, 2013.
International Application No. PCT/US2021/036100, filedJun. 7, 2021 (86 pages).
International Patent Application No. PCT/US2021/032162, filed May 13, 2021 (58 pages).
International Patent Application No. PCT/US2021/036102, filed Jun. 7, 2021 (67 pages).
International Patent Application No. PCT/US2021/070166, filed Feb. 19, 2021 (79 pages).
Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).
Jones, D., "Measure Axial Length to Guide Myopia Management," Review of Myopia Management, 5 pages (Apr. 9, 2020).
Kur, Joanna, et al., "Light adaptation does not prevent early retinal abnormalities in diabetic rats," Scientific Reports, 8 pages (Feb. 8, 2016).
Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).
Lam, Carly Siu Yin, et al., "Defocus Incorporated Multiple Segments (DIMS) spectacle lenses slow myopia progression: a 2-year randomised clinical trial," Br. J Ophthalmol 0:1-6 (2019).
Leo, Seo-Wei, et al., "An evidence-based update on myopia and interventions to retard its progression," J AAPOS, 15(2):181-189 (Apr. 2011).
Lingley, A.R., et al, : A single pixel wireless contact lens display, in J Micromech. Microeng., 2011; 21, 125014; doi:10.1088/0960-1317/21/12/125014, Abstract Only.
Martin, J.A., et al., "Predicting and Assessing Visual Performance with Multizone Bifocal Contact Lenses," Optom Vis Sci, 80(12):812-819 (2003).
Matkovic, K., et al., "Global Contrast Factor—a New Approach to Image Contrast," Computational Aesthetics in Graphics, Visualization and Imaging, 9 pages (2005).
McKeague C, et al. "Low-level night-time light therapy for age-related macular degeneration (ALight): study protocol for a randomized controlled trial", in Trials 2014, 15:246, http://www.trialsjournal.com/content/15/1/246.
Moreno, I, "Creating a desired lighting pattern with an LED array" in Aug. 2008, Proceedings of SPIE—The International Society for Optical Engineering 7058, DOI: 10.1117/12.795673.
Moreno, I., "Modeling the radiation pattern of LEDS", in Optics Express, 2008; 16, 3 pp. 1808.
Nickla, Debora L., et al., "Brief hyperopic defocus or form deprivation have varying effects on eye growth and ocular rhythms depending on the time-of-day of exposure," Exp Eye Res. 161:132-142 (Aug. 2017).
Ramsey, DJ, and Arden, GB, "Hypoxia and dark adaptation in diabetic retinopathy: Interactions, consequences and therapy", in Microvascular Complications-Retinopathy (JK Sun, ed.), Cur Dab Rep (2015) 15: 118, DOI 10.1007/s11892-015-0686-2, Abstract Only.
Read, Scott A., et al., "Choroidal changes in human myopia: insights from optical coherence tomography imaging," Clin Exp Optom, 16 pages (2018).
Read, Scott A., et al., "Human Optical Axial Length and Defocus," IOVS, 51(12):6262-6269 (2010).
Shivaprasad, S, et al, "Clinical efficacy and safety of a light mask for prevention of dark adaptation in treating and preventing progression of early diabetic macular oedema at 24 months (CLEOPATRA):

(56) References Cited

OTHER PUBLICATIONS a multicentre, phase 3, randomised controlled trial," in www.thelancet.com/diabetes-endocrinology vol. 6, pp. 382-391 ( May 2018).
Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).
Srinivasan, S., "Ocular axes and angles: Time for better understanding," J. Cataract Refract. Surg., 42:351-352 (Mar. 2016).
Torii, Hidemasa, et al., "Violet Light Exposure Can Be a Preventive Strategy Against Myopia Progression," EBioMedicine 15:210-219 (2017).
U.S. Appl. No. 17/304,666, filed Jun. 24, 2021 (67 pages).
U.S. Appl. No. 17/302,479, filed May 4, 2021 (60 pages).
U.S. Appl. No. 17/302,827, filed May 13, 2021 (52 pages).
International Search Report and Written Opinion for International Patent Application No. PCT/US2021/036102, 9 pages (Sep. 24, 2021).

\* cited by examiner

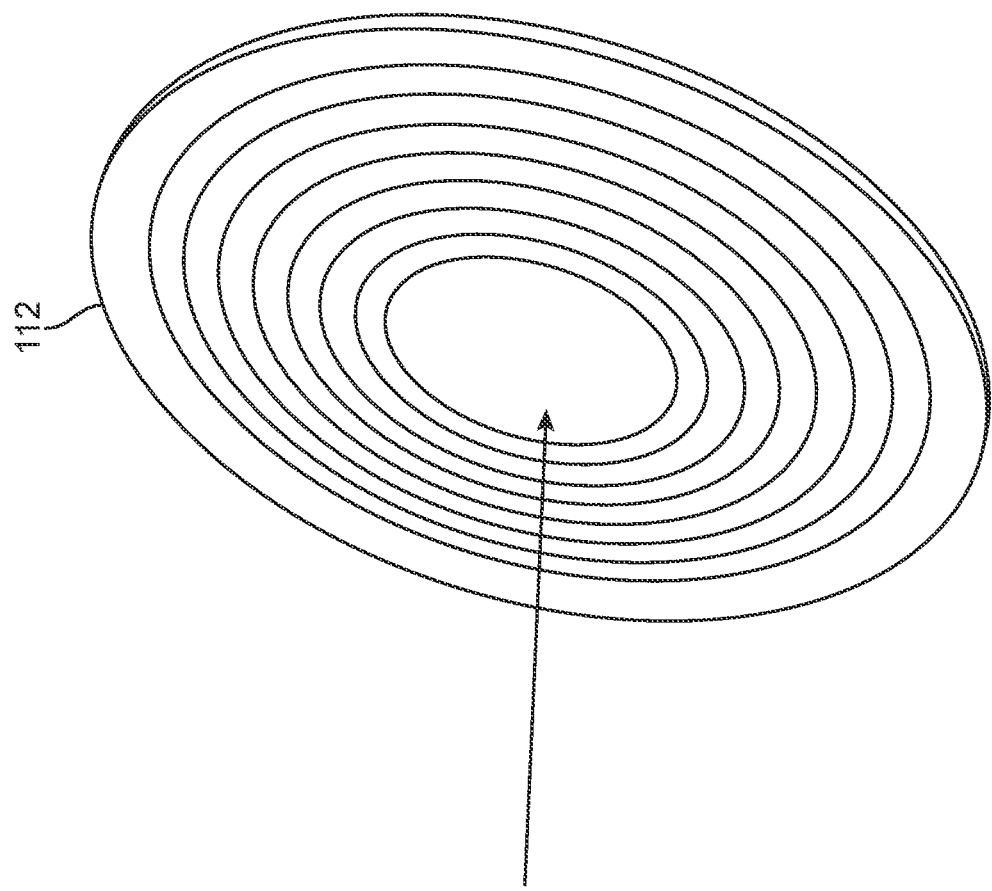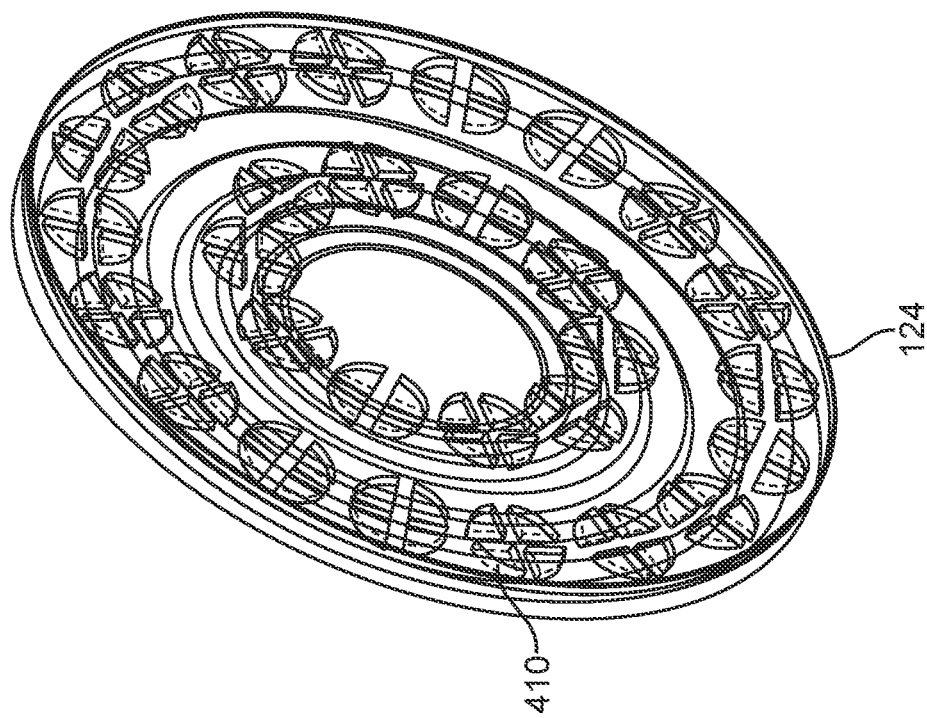
FIG. 5

STICK ON DEVICES USING PERIPHERAL DEFOCUS TO TREAT PROGRESSIVE REFRACTIVE ERROR

RELATED APPLICATIONS

This application is a continuation of International Application No. PCT/US2021/036102, filed Jun. 7, 2021, published as WO 2021/252320 on Dec. 16, 2021, which application claims the benefit under 35 U.S.C. § 119(e) of U.S. Provisional Patent Application No. 63/036,234, filed Jun. 8, 2020, and titled "STICK ON DEVICES USING PERIPHERAL DEFOCUS TO TREAT PROGRESSIVE REFRACTIVE ERROR," which are incorporated, in their entirety, by this reference.

The subject matter of the present application is related to PCT/US2019/043692, filed on Jul. 26, 2019, entitled "ELECTRONIC CONTACT LENS TO DECREASE MYOPIA PROGRESSION", published as WO 2020/028177 A1 on Feb. 6, 2020, the entire disclosure of which is incorporated herein by reference.

BACKGROUND

Prior approaches to treating refractive error such as myopia can be less than ideal in at least some respects. Spectacle lenses, contact lenses, and refractive surgery can be used to treat refractive errors of the eye. However, lenses must be worn in order to correct the errors, and uncorrected refractive error can impact a person's ability to achieve and fully participate in school, sports, and other activities. Although surgery can be performed to decrease refractive error, and surgery comes with risks, such as infection and degraded vision in at least some instances. Also, these approaches do not address the underlying changes in the length of the eye that is related to refractive error such as myopia.

Work in relation to the present disclosure suggests that the retina of many species, including human beings, responds to defocused images and is repositioned through scleral remodeling, in order to decrease the blur caused by the defocus. The mechanism of the generation of the growth signal is still under study, but one observable phenomenon is an increase in thickness of the choroid. A defocused image can cause the choroid thickness to change, which is related to the axial length of the eye. Changes to the axial length of the eye can alter the refractive error by changing the position of the retina in relation to the cornea. For example, an increase axial length increase myopia of an eye by increasing the distance between the cornea and lens.

While the defocus of images can play a role in choroidal thickness and changes in the axial length of the eye, the prior approaches are less than ideally suited to address to refractive error of the eye related to axial length. Although pharmaceutical treatments have been proposed to treat myopia associated with axial length growth, these treatments can have less than ideal results and have not been shown to safely treat refractive error at least some instances. Although light has been proposed as a stimulus to alter the growth of the eye, at least some of the prior devices can provide less than ideal results. Also, the time of treatment can be longer than would be ideal, and at least some of the prior approaches may be more complex than would be ideal.

Therefore, new approaches are needed to treat refractive error of the eye that ameliorate at least some of the above limitations of the prior approaches.

SUMMARY

An apparatus to treat refractive error of an eye comprises an optic comprising an optical zone and a peripheral defocus optical structure to form images of a plurality of stimuli anterior or posterior to a peripheral portion of a retina of the eye. In some embodiments, the peripheral defocus optical structure located outside the optical zone. In some embodiments, the peripheral defocus optical structure comprises optical power to focus light to a different depth of the eye than the optical zone. In some embodiments, the optic comprises one or more of a lens, an optically transparent substrate, a beam splitter, a prism, or an optically transmissive support.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 5 shows assembly of the apparatus of FIG. 2 onto a lens, in accordance with some embodiments;

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus can be configured in many ways to provide retinal stimulation as described herein. The presently disclosed methods and apparatus are well suited for combination with many prior devices such as, one or more of an ophthalmic device, a TV screen, a computer screen, a virtual reality ("VR") display, an augmented reality ("AR") display, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. Although specific reference is made to spectacles and contact lenses, the presently disclosed methods and apparatus are well suited for use with any of the aforementioned devices, and a person of ordinary skill in the art will readily appreciate how one or more of the presently disclosed components can be interchanged among devices, based on the teachings provided herein.

Although the presently disclosed methods and apparatus can be used to treat many types of refractive error, the presently disclosed methods and apparatus are well suited to treat the progression of myopia, for example.

Figure 1:
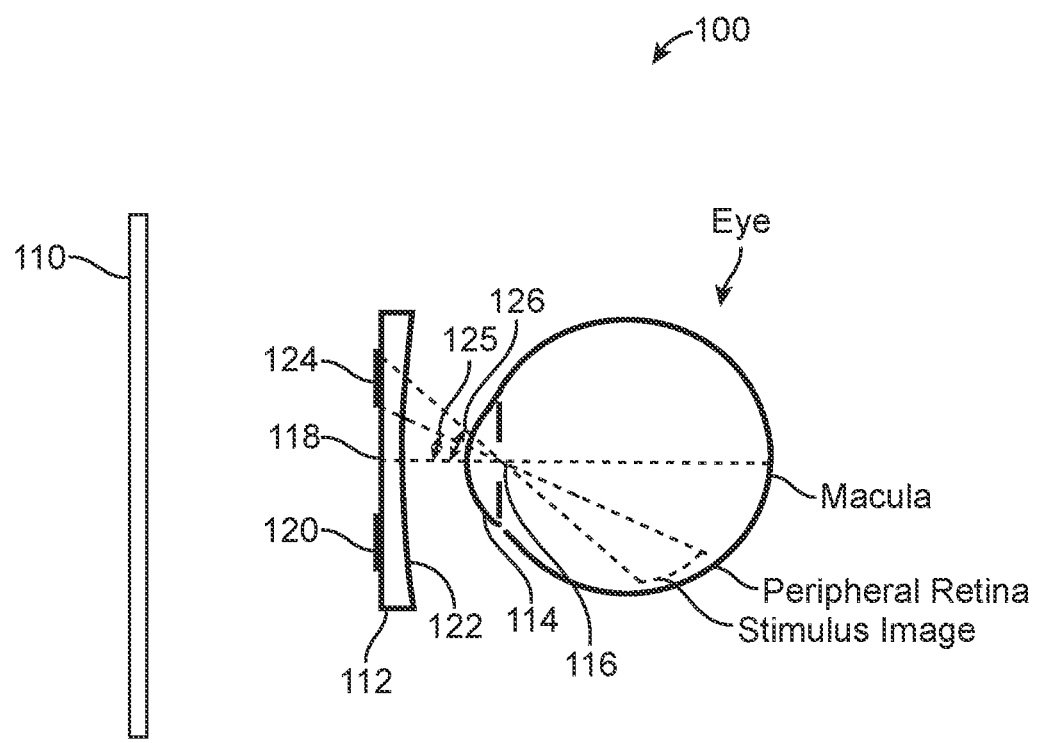
FIG. 1 shows a side view of a vision apparatus to treat refractive error of an eye, in accordance with some embodiments.

FIG. 1 shows a cross section of an apparatus 100 to treat refractive error of an eye. The apparatus 100 may comprise any suitable vision device, such as a VR headset. The components of the apparatus may be arranged with reference to the eye of a user. The apparatus 100 such as a VR headset may comprise a display 110. The display 110 provides visual content, such as video games and movies for viewing by a user. The images of the display 110 are transmitted through the optic 112 to the eye of the user, represented by the cornea 114 and the pupil 116. The optic 112 may comprise a refractive lens that changes the focus of the light before the light enters the eye of a user. Alternatively, the optic may comprise flat surfaces, such as a beam splitter, or a prism for example. The optic 112 may include a posterior optical structure 122 that may be curved or otherwise shaped to adjust the focus of the projected image from the display 110 onto the user's eye. For example, in apparatus 100 such as a VR device, the posterior optical structure 122 may comprise a Fresnel lens. In other devices, for example in spectacles, the optic 112 may comprise a prescription lens to correct refractive errors of the patient's eye with the posterior optical surface 122 shaped to correct one or more of myopia, hyperopia, astigmatism, and other refractive errors of the eye. Although reference is made to a Fresnel lens, the lens may comprise any suitable lens structure, such as one or more of a curved lens, a toric lens, a Fresnel lens, a diffractive, or a holographic element, and combinations thereof.

A defocus treatment device 124 may be attached or part of a surface of the optic 112. For example, in FIG. 1 the defocus treatment device 124 is a part of, or attached to, the front surface of the optic 112. In some embodiments, the treatment device 124 is adhered to the optic 112 with an adhesive. In some embodiments, the defocus treatment device 124 comprises a peripheral defocus optical structure 120 arranged around a central optical zone 118. In some embodiments, the central optical zone is configured to provide a clear field of view of an object such as the display 110. The optical zone can be configured in many ways, and may comprise an optical zone with correction to provide the eye with an unobstructed in focus image of the display on the macula of the retina of the eye. In some embodiments, the defocus optical structure 120 alters the focus of the light. The defocus optical structure can be configured to form an image of a stimulus anterior to the retina to treat refractive error of the eye such as myopia. Alternatively, the image of the stimulus can be formed posterior to the retina of the eye. The image of the stimulus may comprise an image of a stimulus on the display, for example. Although reference is made to the treatment defocus device adhered to the lens 112, in some embodiments the defocus optical structure 120 is formed directly on the surface of lens 112, for example with structures etched into the surface of lens 112.

The dimensions of the optical zone 118 and peripheral defocus optical structure 120 zone can be configured in many ways. In some embodiments, the peripheral defocus optical structure 120 is sized and shaped to transmit light at an angle within a range from 12 degrees to 40 degrees with reference to an entrance pupil of the eye or within a range from 15 to 35 degrees, for example. In some embodiments, the angle comprises a half-angle, such as an angle between the boundary of the optical zone and a line formed through the center of the optical zone and the center of the entrance pupil. In some embodiments, the peripheral defocus optical structure 120 is sized to be at an angle within range from 15 degrees to 50 degrees with reference to an entrance pupil of the eye, for example. In some embodiments, the peripheral defocus optical structure 120 comprises an inner boundary and an outer boundary. The inner boundary corresponding to an inner boundary angle 125 within a range from 15 degrees to 20 degrees with reference to the entrance pupil 116 of the eye and the outer boundary corresponding to an outer boundary angle 126 within a range from 25 degrees to 70 degrees with reference to the entrance pupil of the eye. In some embodiments, the lens is a distance from the eye. The distance, the inner boundary, and the outer boundary may be dimensioned to provide the inner angle and the outer angle with reference to the entrance pupil of the eye.

The peripheral defocus optical structure 120 may be annular in shape, having an inner diameter and an outer diameter selected such that the peripheral defocus is applied to a portion of the retina of the patient's eye that is eccentric to the fovea. For example, the inner diameter may be at an angle of about 7.5 degrees with respect to an optical axis of the optic 112 and pupil, this angle may be referred to as an inner boundary angle 125. The outer diameter of the peripheral defocus optical structure 120 may be at an outer boundary angle 126 with respect to the optical axis of the primary eye and the people, for example at 17.5 degrees. Such an arrangement, results in the peripheral defocus optical structure 120 being located in a peripheral field of view of the user with a corresponding defocus of the projected light in a peripheral region of the user's retina eccentric to the fovea.

Although reference is made to an annular shape, the peripheral defocus optical structure 120 can be configured with other shapes, such as polygons, squares, triangles, and may comprise a plurality of discrete optical structures located around the optical zone at appropriate locations.

In some embodiments, the peripheral defocus optical structure 120 may include optics or optical structures that change the focus of the projected light in the patient's eye. Peripheral defocus optical structure 120 may comprise one or more of diffractive optics, lenslets, gradient index ("GRIN") lenslets, crossed cylindrical rods, masks, or echelettes that alter the focus of light passing through the defocus optical structure 120.

In some embodiments, the peripheral defocus optical structure 120 is dimensioned to provide defocused images to a peripheral portion of the retina. In some embodiments, the defocus optical structure 120 is configured to provide a stimulus to a peripheral portion of the retina that comprises a region of the retina outside the fovea or the macula, so as to provide clear vision to the fovea and the macula when the user looks ahead and the peripheral defocus optical structure 120 provides a defocused image onto the peripheral retina. The image may be defocused in a range between 2.0 to 6.0 Diopters ("D") myopically or hyperopically with respect to the retina. For example, the defocus may be 3.5 to 5 D anterior to the retina, e.g. myopic defocus, or posterior to the retina, e.g. hyperopic defocus. The defocus is preferably between 2.5 to 5.0 D, and more preferably between 3.0 to 5.0 D.

In some embodiments, a defocus treatment device may be used in combination with localized stimuli projected by a display into the peripheral zone to treat refractive errors of the eye. In the defocus treatment device 124, the stimuli along with the video content projected by a display, are projected through the peripheral defocus optical structure 120 and accordingly both the image of the video content and the stimuli are defocused by the peripheral defocus optical structure.

For the treatment of spherical refractive errors of the eye, such as myopia, the stimulation projected to the retina may be uniform about the periphery of the central optical zone 118. For the treatment of cylindrical refractive errors of the eye, such as astigmatism, the stimulation projected to the retina may be non-uniform about the periphery of the central optical zone 118. For example, the stimulation may be greater along a meridian corresponding to or aligned with an astigmatic first axis of the eye and symmetrically mirrored about a second astigmatic axis of the eye.

Figure 2:
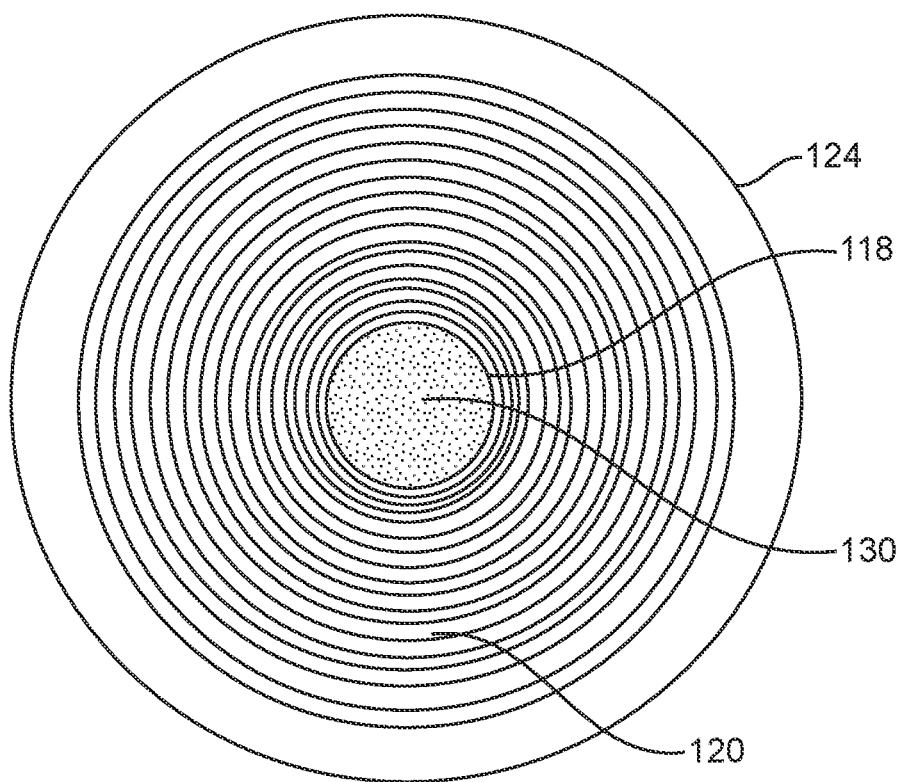
FIG. 2 shows an apparatus to treat refractive error of an eye, in accordance with some embodiments.

FIG. 2 depicts a defocus treatment device 124 with a hardware-based defocus structure and stimuli provided by software, such as software that modifies the image projected from the display such that the image includes appropriate stimuli. The defocus treatment device 124 includes a central optical zone 118 and a peripheral defocus optical structure 120. The central optical zone 118 may be plano such that it has substantially planar surfaces or may otherwise be shaped such that it provides little to no change in the angle of the incident light passing through the central optical zone 118. Although reference is made to the central optical zone comprising substantially planar surfaces, the central optical zone my comprise optical power to correct refractive error of the eye, or combined with optical correction such as spectacles. The central optical zone 118 may also include a filter 130 such as a neutral density filter or mask.

In some embodiments, the neutral density filter is provided in order to increase the intensity of the stimuli in relation to the central clear vision zone, so as to provide increased stimulation to the outer portions of the retina, e.g. the peripheral retina. In some embodiments, a neutral density filter comprises a filter that substantially equally reduces or modifies the intensity of light in the visible wavelengths without inducing changes in the hue or color of the light passing through the filter. The neutral density filter may reduce the illumination of the light by 80% to 99%, preferably between 90 and 95%, more preferably about 97%. The neutral density filter 130 may provide a difference in illumination between the central optical zone 118 or other filtered areas and the outer zone or other non-filtered areas of at least a factor of 5, preferably at least a factor of 10, 20, or 30. In some embodiments, the illumination difference provided by the neutral density filter and non-filtered areas of the defocus treatment device 124 may be a factor of about 5, 10, 20, or 30. In some embodiments the illumination difference may be between a factor of 5 and 30, more preferably between a factor of 10 and 20. Although reference is made to a neutral density filter, in some embodiments the filter 130 comprises a tinted filter.

In some embodiments, the outer area of the defocus treatment device 124 includes a peripheral defocus optical structure 120. The peripheral defocus optical structure 120 may be provided by a Fresnel lens as shown in FIGS. 2, 3A, 3B, 4, and 5, or any suitable optical structure as described herein. The Fresnel lens is dimensioned to provide defocused images to a peripheral portion of the retina. In some embodiments, the peripheral portion of the retina comprises a region of the retina outside the fovea or the macula, and defocus is provided to this area while the central area is not defocused so as to provide clear vision to the fovea and the macula when the user looks ahead. The Fresnel lens of the defocus optical structure 120 may have an optical power within a range from 2.0 D to 6.0 D myopically or hyperopically. For example, the optical power may be within a range from 3.5 D to 5 D myopically or hyperopically. In some embodiments, the optical power is preferably within a range from 2.5 D to 5.0 D, and more preferably within a range from 3.0 D to 5.0 D.

The peripheral defocus optical structure 120 may be annular in shape having an inner diameter and an outer diameter selected such that the peripheral defocus is applied to a portion of the retina of the patient's eye that is eccentric to the fovea. For example, the inner diameter may be selected such that it is at an angle of about 7.5 degrees with respect to an optical axis of the optic 112 and pupil. The outer diameter of the peripheral defocus optical structure 120 may be at an outer boundary angle with respect to the optical axis of the primary eye and the people, for example at 17.5 degrees. Such an arrangement results in the peripheral defocus optical structure 120 being located in a peripheral field of view of the user with a corresponding defocus of the projected light in a peripheral region of the user's retina eccentric to the fovea.

In some embodiments, a defocus treatment device may be used in combination with localized stimuli in the peripheral zone to treat refractive errors of the eye. The localized stimuli may be part of a projected image, for example from a display, or may be provided by structure within or a part of the defocus treatment device.

Figure 3:
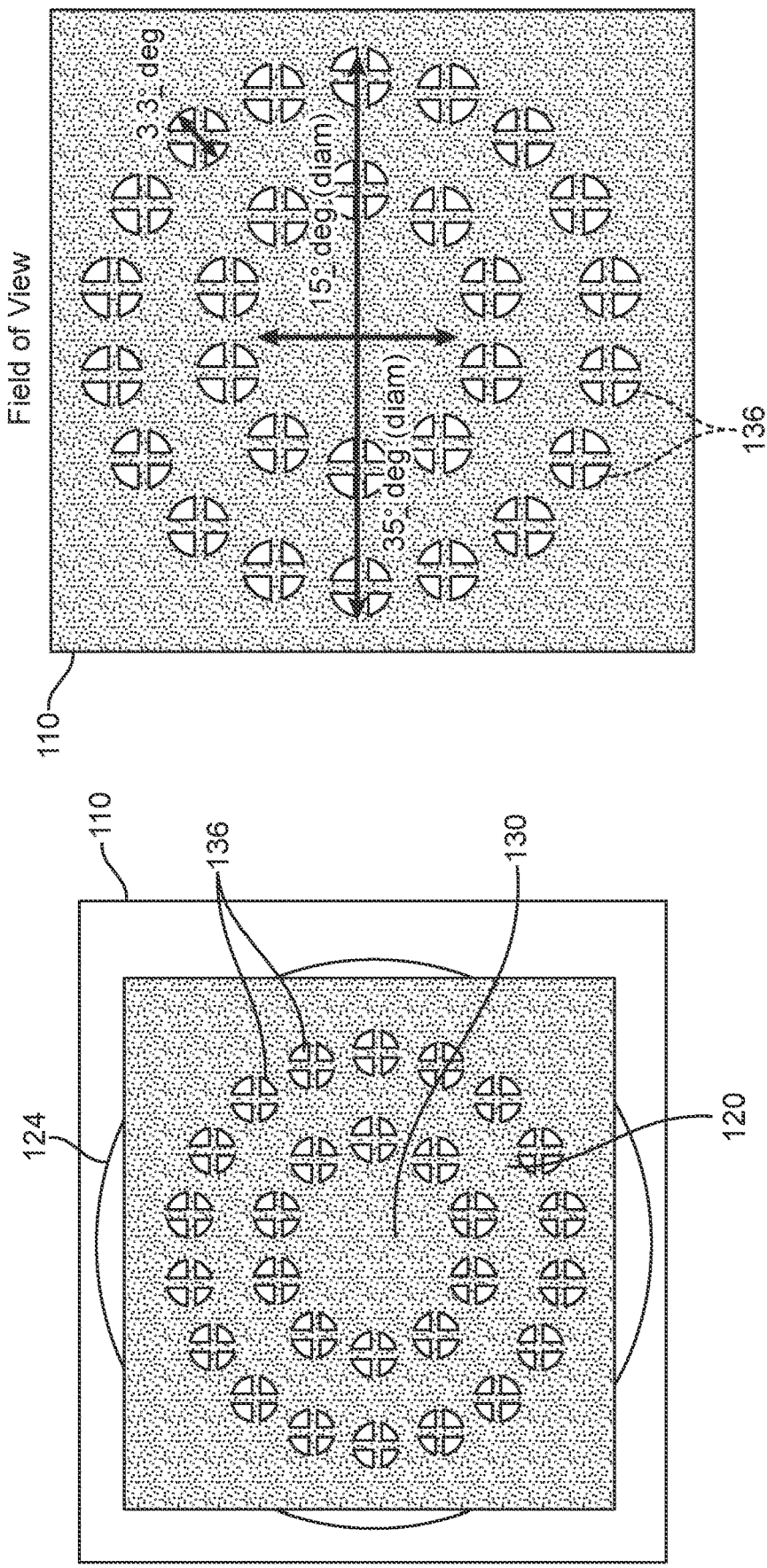
FIG. 3A shows the apparatus of FIG. 2 in use, in accordance with some embodiments.
FIG. 3B shows a display with a plurality of stimuli and the corresponding dimensions of the defocused stimuli on the retina in degrees, in accordance with some embodiments.

For example, FIG. 3A depicts defocus treatment device 124 in front of a display 110. The display 110 may provide video or other image content for projection through the defocus treatment device 124 and into the eye of a user. As discussed above, the defocus treatment device 124 may be placed anterior to the optic 112, such as a lens of a virtual reality headset or eyeglasses or other devices worn by user.

FIG. 3B shows the display 110 with a plurality of stimuli and the corresponding dimensions of the defocused stimuli on the retina in degrees. The size of the stimuli on the display is related to the distance between the user and the display, and the dimensions can be changed in accordance with the viewing distance to provide an appropriate angular subtense to the retina. One of ordinary skill in the art can readily perform calculations to determine the size of and locations of the stimuli on the display to provide appropriate angular sizing of the defocused projected images. Each of the stimuli comprises a distance across corresponding to an angular illumination on the retina, for example 3.3 degrees. The stimuli are arranged to provide a clear central field of view, which can be 15 degrees, for example. The plurality of stimuli comprises a maximum distance across, e.g. 70 mm, which corresponds to an angular subtense of 35 degrees.

In the embodiments shown in FIGS. 3A and 3B, the video content or other imagery provided by the display 110 may be modified to include stimuli 136. The stimuli 136 may be provided in the form of increased luminosity or brightness at locations eccentric to the center of the image on the display. The stimuli 136 can be positioned on the display 110 to provide stimulation to peripheral regions of the retina when passed through the defocus optical structure 120. In some embodiments, a processor is configured with instructions to place the stimuli 136 at locations on the display corresponding to locations on the retina. The display 110 can be located at an appropriate distance from the defocus optical structure 120 so as to form image the stimuli 136 anterior or posterior to the retina as described herein.

The stimuli may be located in fixed locations or within a range from the center of the display 110. In some embodiments, such a spatial arrangement of stimuli within the display may provide stimulation in substantially fixed locations on the retina of a user because the display, the defocus treatment device, in the user's eyes are maintained in a substantially fixed arrangement by the mounting of the headset to the patient's head, e.g. with a VR or AR headset. In some embodiments, the headset may include an eye tracker that tracks the location and/or the orientation of the user's eye. The location of the stimuli on the display may be updated based on the location and/or the orientation of the user's eye. In some embodiments, the peripheral stimuli may be turned on or off based on the position of the user's eye. For example, in some embodiments, the user's eye may be at a point of regard such that the stimuli might appear within the user's central vision. In such embodiments, stimuli that would otherwise appear within the user's central vision may be deactivated when the eye tracker detects that the stimulation might be within the user's central vision.

The stimuli may be sized such that they are about 0.5 to 5 degrees in apparent diameter in the field of view of a user, more preferably about 2 to 3 degrees, and most preferably about 2.3 degrees.

The one or more stimuli may include images configured in many ways and may include an image structure corresponding to information or content associated with spatial frequencies. In some embodiments, the one or more images projected in the stimuli comprises a spatial frequency within a range from 1 cycle per degree to 180 cycles per degree, and a contrast within a range 99.9% to 2.5%, for example. In some embodiments, the projected image comprises image structure content configured to provide a range of spatial frequencies, for example within a range from 2 cycles per degree to about 60 cycles per degree. In some embodiments, the image is projected onto the retina with a modulus of an optical transfer function that is equal to or better than 0.3 at a spatial frequency of 50 lp/mm or greater.

In some embodiments, the stimuli may include a darker area within a brighter area or a brighter area within a darker area. For example, as shown in FIGS. 3A and 3B, each of the plurality of stimuli may include a bright circular area with a dark cross shape inscribed within. The cross shape may include two dark lines intersecting perpendicular to each other, for example, at their midpoints and at the center of the bright circle. In some embodiments, the stimuli may include a single line extending across the diameter of the circle.

In the defocus treatment device 124, the stimuli 136 along with the video content projected by the display 110 are projected through the peripheral defocus optical structure 120 and accordingly both the image of the video content and the stimuli 136 are defocused by the peripheral defocus optical structure 120.

Figure 4:
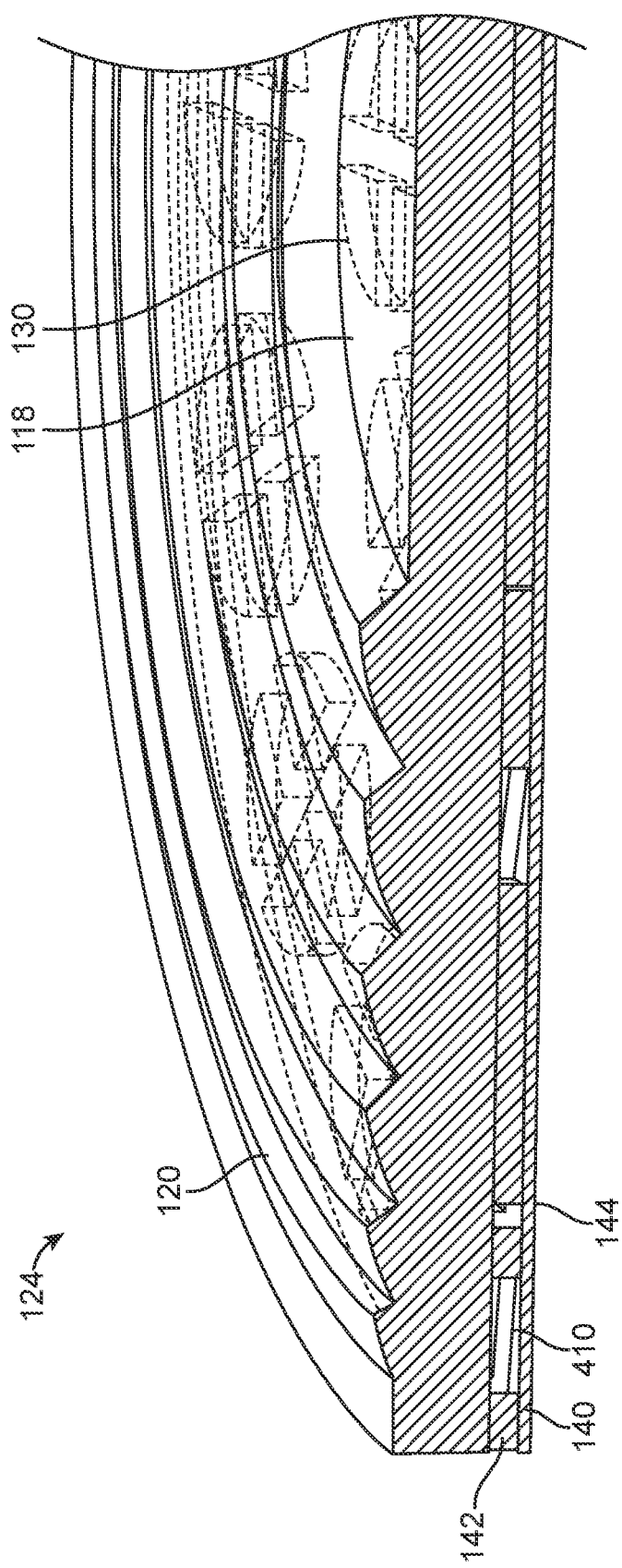
FIG. 4 shows a cross-sectional perspective view of the apparatus of FIG. 2, in accordance with some embodiments.

FIG. 4 shows a cross-section of defocus treatment device 124, including the plano center area 118 and the peripheral defocus optical structure 120. As shown in FIG. 4 the peripheral defocus optical structure 120 may be a Fresnel lens or other suitable optical structure with a first curved surface having a shape according to the desired diopter of the lens and a second surface that may be slanted with respect to the optical axis of the lens, as shown in FIG. 4, or may be perpendicular to the optical axis of the lens. The peripheral defocus optical structure for may have other shapes or structures. For example, the peripheral defocus optical structure may be a diffractive optical structure, an echelette, or a series of concentric annular lenses having a curved surface of the desired diopter.

As further shown in FIG. 4, the defocus treatment device 124 may include one or more of filter 130 or a filter or mask layer 142. In some embodiments, the layer 142 comprise a neutral density layer, although the layer may be tinted or clear, for example. The neutral density layer 142 may include a neutral density filter in the areas of the lens that are desired to be darker and have lower illumination. The neutral density filter may be located on a posterior surface of the defocus treatment device 124 opposite an anterior surface on which the peripheral defocus optical structure 120 is located. The neutral density filter layer 142 may be located about the plano center optical zone 118 such that light passing through the plano center optical zone 118 also passes through the neutral density filter. In some embodiments, the neutral density filter layer 142 may extend about the peripheral defocus optical structure 120 such that a portion of the light passing through the peripheral defocus optical structure 120 is filtered by the neutral density filter layer 142. As further shown in FIG. 4, peripheral stimuli may be provided, at least in part, by one or more locations on the defocus treatment device 124 not subject to filtering by the neutral density filter layer 142. Structures 410 may be formed in or through the neutral density filter layer 142 to allow unfiltered light to pass through. For example, in FIG. 4 the defocus treatment device 124 includes a neutral density filter layer 142 and stimuli locations with structures 410 formed to allow unfiltered light to pass through. The structures 410 may be of any suitable shape as described herein, for example so as to form a bright circular area with a dark cross shape inscribed within. The structures 410 may comprise one or more of a transparent material, or apertures for example. The cross shape may include two dark elongated structures formed by the neutral density filter that intersect perpendicular to each other at their midpoints and at the center of the circle. In some embodiments, the stimuli may include a single line formed by the neutral density filter layer 142 that extends across the diameter of the circle. Although reference is made to a cross shape, the structures 410 may comprise any suitable shape to provide a stimulus as described herein.

In some embodiments, neutral density filter 130 may extend beyond the central plano region of the defocus treatment device 124. For example, the neutral density filter 130 may extend to encompass the peripheral defocus optical structure 120. In some embodiments, the region of the defocus treatment device 124 that includes the peripheral defocus optical structure 120 may include portions masked by the neutral density filter 130 and portions not masked by the neutral density filter 130. The unmasked or clear portions of the outer area may be clear and optically aligned with stimuli provided in the image or video content of the display 110. When optically aligned, the unmasked portions of the outer area and the stimuli appear superimposed over each other from the perspective of the user. By combining increased luminosity from the stimuli in the projected image with the difference in luminosity of masked and unmasked regions of the defocus treatment device, a greater difference between the luminosity of the stimuli as compared to non-stimulated regions may be provided.

With reference to FIG. 4 and FIG. 5, the defocus treatment device 124 may include a clear base 140 on a posterior side of the defocus treatment device 124. The base 140 may include a lens interface surface 144 for coupling the defocus treatment device 124 to a lens, such as lens 112. In some embodiments, the lens interface surface 144 may include an adhesive to further facilitate coupling the defocus treatment device 124 to a lens or other structure. In some embodiments, the defocus treatment device 124 may be formed directly on or in a lens. In such embodiments, the defocus treatment device 124 may not have a base 140 on an anterior surface or the base 140 may be the optical structure such as the lens 112.

Figure 6:
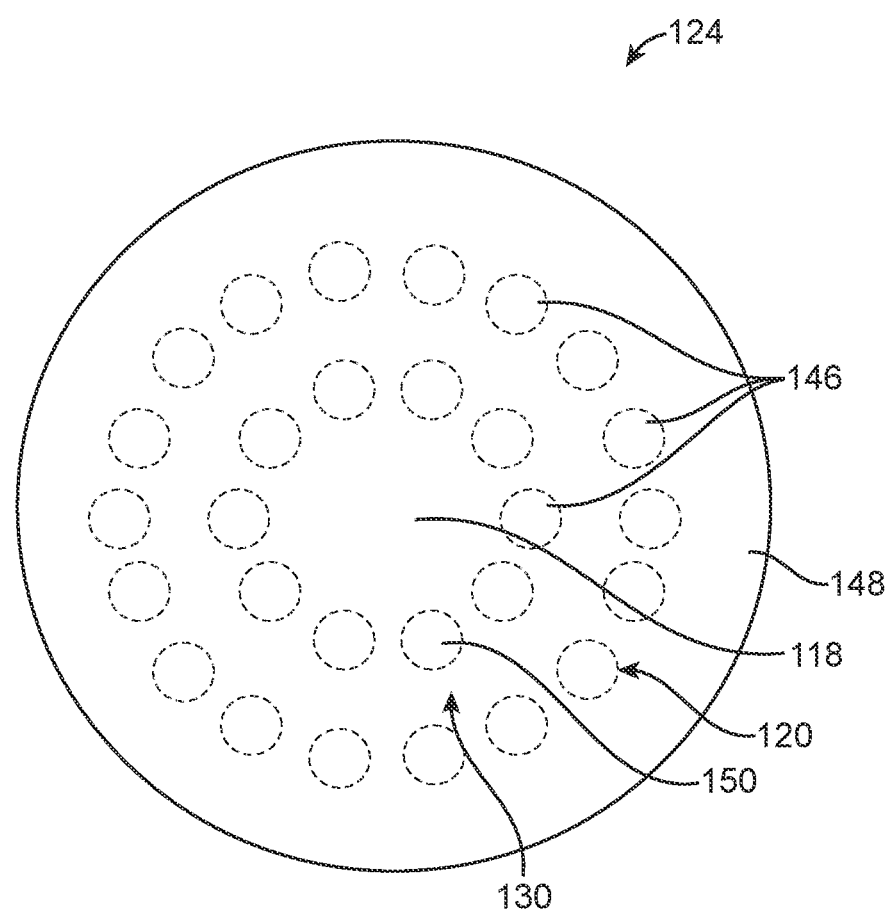
FIG. 6 shows an apparatus to treat refractive error of an eye, in accordance with some embodiments.

FIG. 6 depicts a defocus treatment device 124 with a hardware-based defocus structure and stimuli provided by hardware and optionally by software, such as software that modifies the image projected from a display to include stimuli. The defocus treatment device 124 includes a central optical zone 118. The central optical zone 118 may be plano such that it has substantially planar surfaces or may otherwise be shaped such that it provides little to no change in the angle of the incident light passing through the central optical zone 118. The central optical zone 118 may also include a neutral density filter 130 or mask 150. The defocus treatment device 124 may have a substantially plano anterior surface in non-stimuli areas, for example in areas not including lenslets 146.

The defocus treatment device 124 may also include a neutral density filter 130. The neutral density filter 130 filters light passing through the plano regions of the defocus treatment device 124. In some embodiments, the neutral density filter 130 filters light passing through the defocus treatment device 124 in non-stimulated regions of the defocus treatment device 124.

The outer area of the defocus treatment device 124 includes a peripheral defocus optical structure 120. The peripheral defocus optical structure 120 may include one or more lenses in the outer region of the device 124. For example, the peripheral defocus optical structure 124 may include an array of lenslets 146, as shown in FIGS. 6, 7, 8, 9 and 10. The plurality of lenslets 146 may be shaped and arranged to provide defocused images to a peripheral portion of the retina while providing clear vision to the fovea and the macula when the user looks ahead. The each lenslet 146 of the defocus optical structure 120 may have an optical power within a range range from 2.0 D to 6.0 D myopically or hyperopically. For example, the optical power may be within a range from 3.5 D to 5 D myopically or hyperopically. The curvature is preferably between 2.5 to 5.0 D, and more preferably between 3.0 to 5.0 D.

The lenslets 146 of the peripheral defocus optical structure 120 may be arranged in one or more circular arrays centered about the central optical zone 118 of the defocus treatment device 124. The one or more circular arrays may form an annular shape having an inner diameter and an outer diameter selected such that the peripheral defocus is applied to a portion of the retina of the patient's eye that is eccentric to the fovea. For example, the inner diameter may be selected such that it is at an angle of about 7.5 degrees with respect to an optical axis of the optic 112 and pupil. The outer diameter of the peripheral defocus optical structure 120 may be at an outer boundary angle with respect to the optical axis of the primary eye and the people, for example at 17.5 degrees.

In some embodiments, the location of the lenslets 146 and the unfiltered areas of the defocus treatment device 124 may be positioned with respect to each other such that the light passing through the unfiltered areas of the device 124 also pass through the lenslets 146 such that the unfiltered light is defocused with respect to the patient's retina. A defocus treatment device may be used in combination with localized stimuli in the peripheral zone to treat refractive errors of the eye. The localized stimuli may be part of a projected image, for example from a display, or may be provided by structure within or a part of the defocus treatment device.

Figure 7:
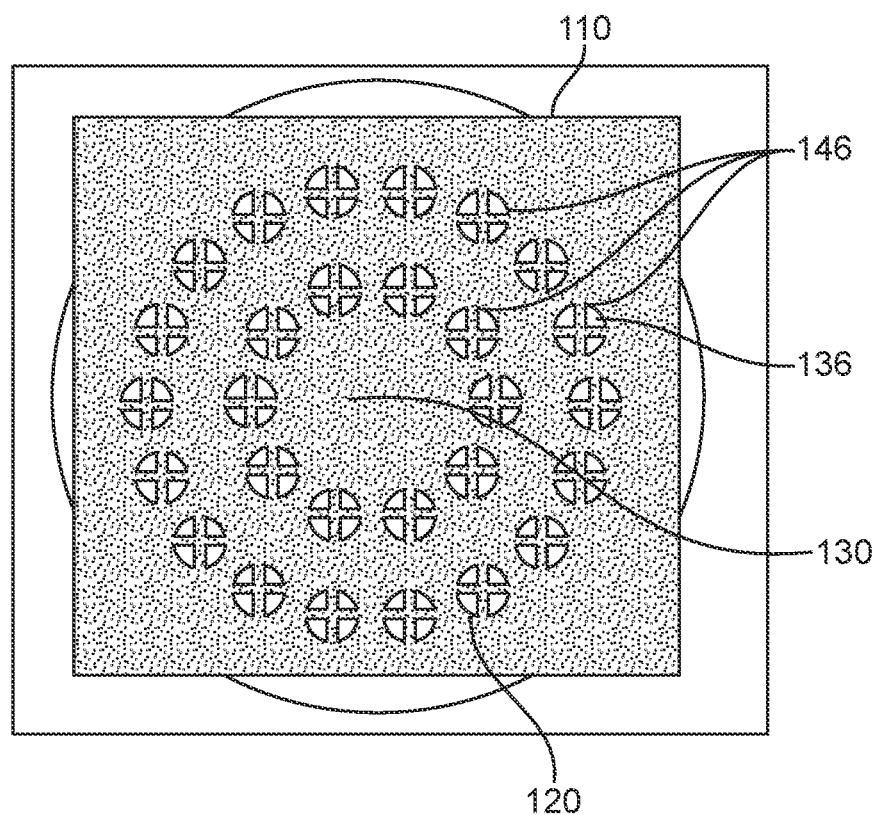
FIG. 7 shows the apparatus of FIG. 6 in use, in accordance with some embodiments.

For example, FIG. 7 depicts defocus treatment device 124 in front of a display 110. The display 110 may provide video or other image content for projection through the defocus treatment device 124 and into the eye of a user. As discussed above, the defocus treatment device 124 may be placed anterior to the optic 112, such as a lens of a virtual reality headset or eyeglasses or other devices worn by user. In the embodiment shown in FIG. 7 the video content or other imagery provided by the display 110 may be modified to include stimuli 136. The stimuli 136 may be provided in the form of increased luminosity or brightness at locations eccentric to the center of the image on the display.

The stimuli may be located in fixed locations or within a range of the center of the display 110. Such a fixed arrangement of stimuli within the display of a VR headset may provide stimulation in substantially fixed locations on the retina of a user because the display, the defocus treatment device, in the user's eyes are maintained in a substantially fixed arrangement by the mounting of the VR headset to the patient's head. In some embodiments, the VR headset may include an eye tracker that tracks the location and/or the orientation of the user's eye. The stimuli and associated lenslets may be sized such that they are about 0.5 to 5 degrees in apparent diameter in the field of view of a user, more preferably about 2 to 3 degrees, and most preferably about 2.3 degrees.

The one or more stimuli may include images configured in many ways and may include an image structure corresponding to information or content associated with spatial frequencies. In some embodiments, the stimuli may include a darker area within a brighter area or a brighter area within a darker area. For example, as shown in FIG. 7, the stimuli may include a bright circular area with a dark cross shape inscribed within. The cross shape may include two dark lines intersecting perpendicular to each other, for example, at their midpoints and at the center of the bright circle. In some embodiments, the stimuli may include a single line extending across the diameter of the circle.

In the defocus treatment device 124, the stimuli 136 along with the video content projected by the display 110 are projected through the peripheral defocus optical structure 120 and accordingly both the image of the video content and the stimuli 136 may be defocused by the peripheral defocus optical structure 120.

Figure 8:
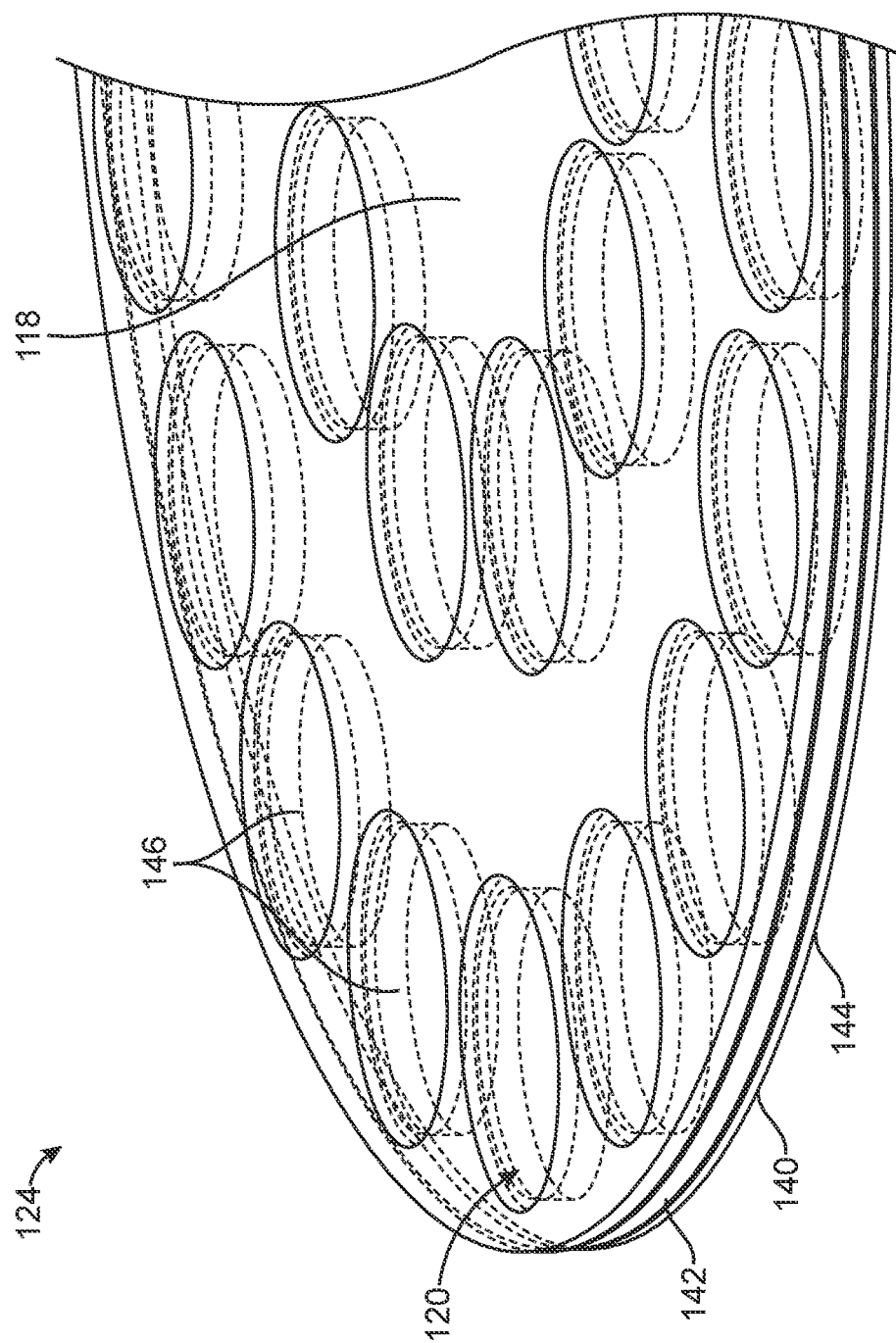
FIG. 8 shows a perspective view of the apparatus of FIG. 6, in accordance with some embodiments.
Figure 9:
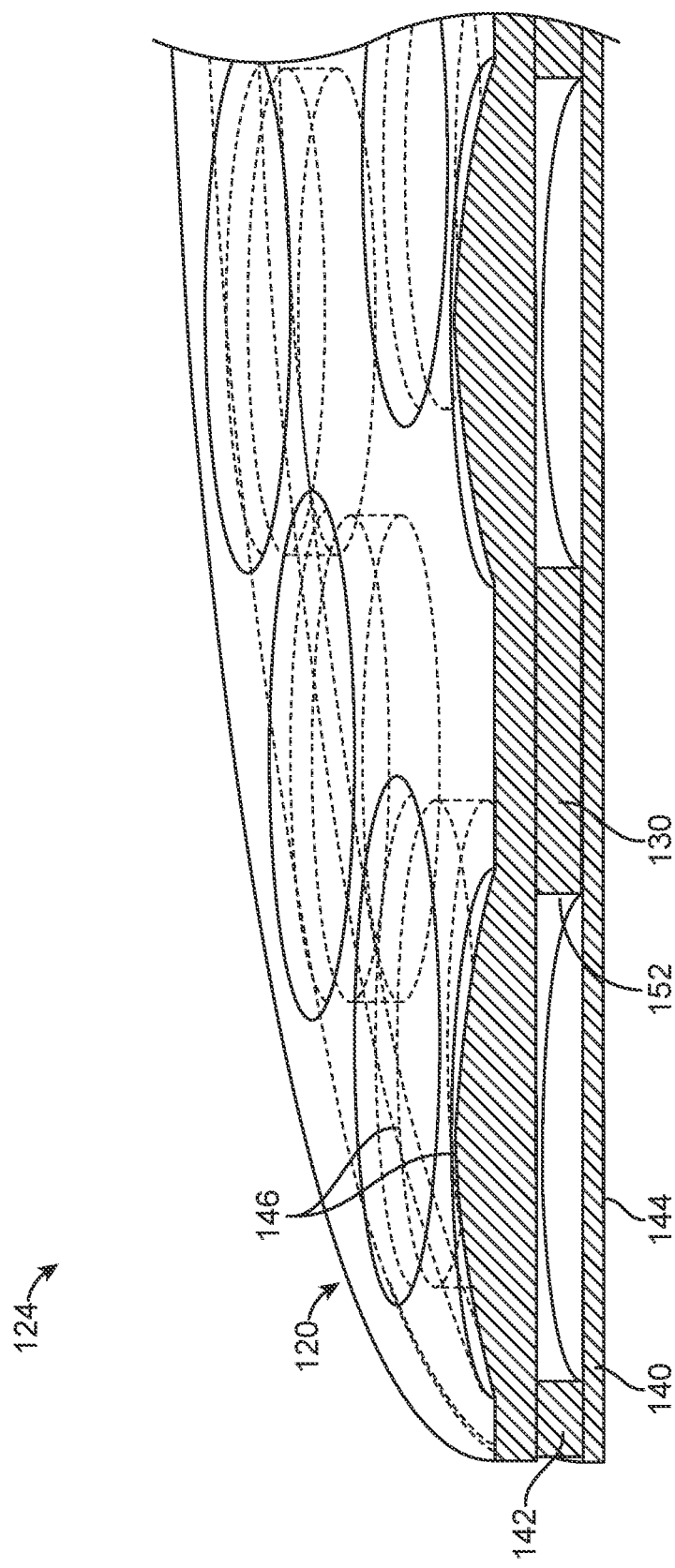
FIG. 9 shows a cross-sectional perspective view of the apparatus of FIG. 6, in accordance with some embodiments.

FIGS. 8 and 9 show a perspective and cross-section of defocus treatment device 124, respectively, including the plano center area 118 and the peripheral defocus optical structure 120. The peripheral defocus optical structure 120 may include a plurality of lenslets 146 each having a curved surface shaped according to the desired diopter in defocus of the lenslets. The lenslets for may have other shapes or structures. For example, lenslets may be formed from one or more of a diffractive optical structures, GRIN lenses, echelettes, holographic lenses, or Fresnel lenses having a shape or structure to create the desired optical. In some embodiments, the lenslets may be electrically tunable lenses that allow for dynamic variation in the defocus provided by the lenslets 146. For example, in some embodiments the lenslets may provide no defocus during certain periods while providing a defocus of 2 to 6 D during other periods.

The defocus treatment device 124 may include filter 130 such as a neutral density filter or mask layer 142. The layer 142 may include a neutral density filter in the areas of the lens that are desired to be darker and have lower illumination. The neutral density filter may be located on a posterior surface of the defocus treatment device 124 opposite an anterior surface on which the peripheral defocus optical structure 120, such as the lenslets 146, is located. In some embodiments, the neutral density filter layer 142 may extend from the plano center 118 and to plano regions of the peripheral defocus optical structure 120 such that a portion of the light passing through the plano regions of the peripheral defocus optical structure 120 is filtered by the neutral density filter layer 142. In some embodiments, the neutral density filter layer 142 may not cover locations of the defocus treatment device 124 corresponding to the locations of lenslets 146. The peripheral stimuli 136 may be provided, at least in part, by one or more locations on the defocus treatment device 124 not subject to filtering by the neutral density filter layer 142. Structures such as apertures or transparent material may be formed in or through the neutral density filter layer 142 to allow unfiltered light to pass through. For example, as shown in the cross-section of FIG. 9, the defocus treatment device 124 includes a neutral density filter layer 142 and stimuli locations with structures formed to allow unfiltered light to pass through. The structures may be of a shape as discussed above such that they form a bright circular area with or without a dark cross shape inscribed within.

The outer perimeter of the aperture formed though the filter 130 may include a light barrier or baffle 152 that aids in preventing light passing through one aperture towards the associated lenslet from entering or scattering through the filter into a different lenslet not associated with the aperture. In some embodiments, the baffle or barrier may extend into or through the optical layer 142 to the lenslet on the anterior surface of the peripheral defocus optical structure 120.

Figure 10:
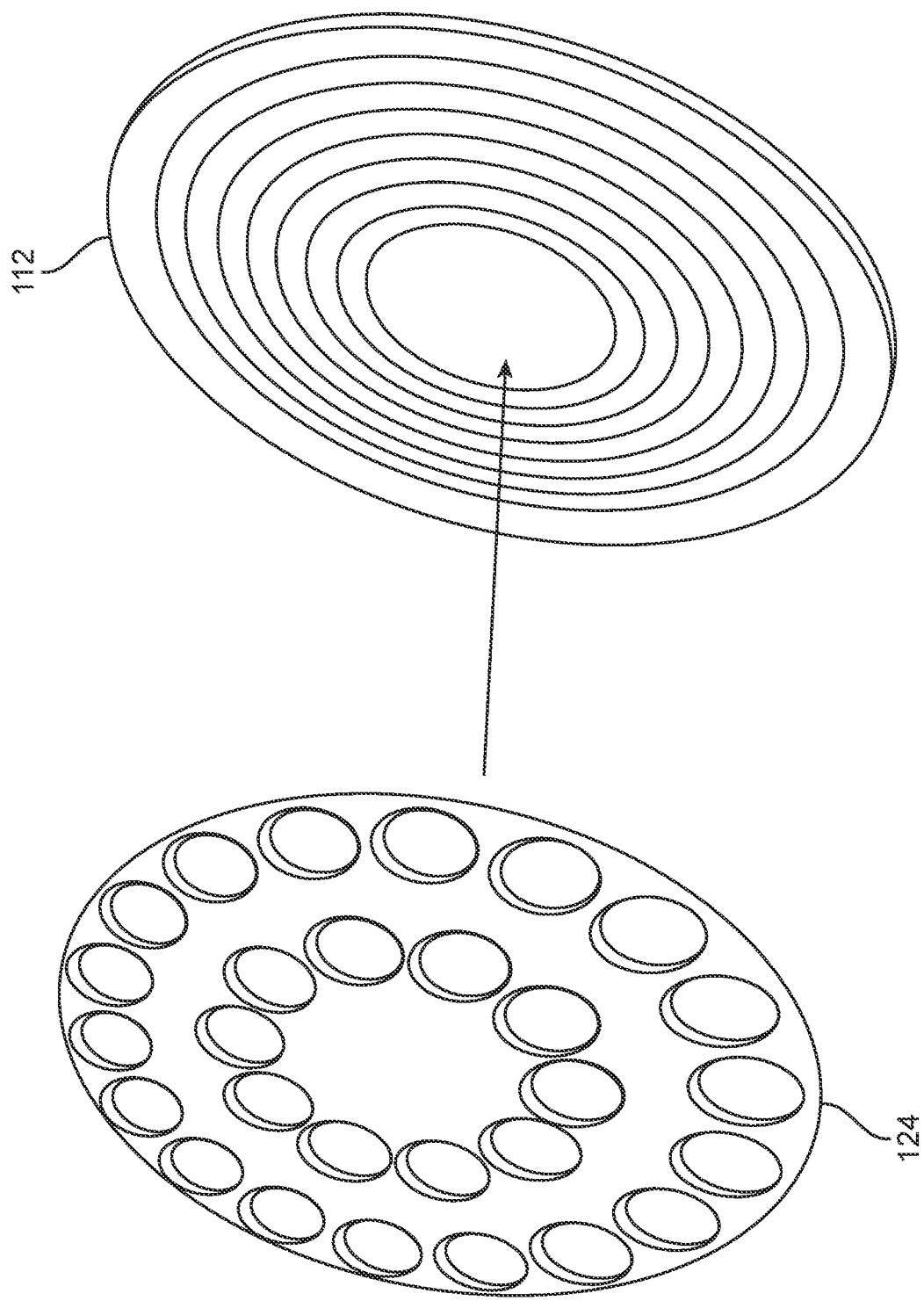
FIG. 10 shows assembly of the apparatus of FIG. 6 onto a lens, in accordance with some embodiments.

With reference to FIGS. 8 to 10, the defocus treatment device 124 may include a clear base 140 on a posterior side of the defocus treatment device 124 the base 140 may include a lens interface surface 144 for coupling the defocus treatment device 124 to a lens, such as lens 112. In some embodiments, the lens interface surface 144 may include an adhesive to further facilitate coupling the defocus treatment device 124 to a lens or other structure. In some embodiments, the defocus treatment device 124 may be formed directly on or in a lens. In such embodiments, the defocus treatment device 124 may not have a base 140 on an anterior surface or the base 140 may be the optical structure such as the lens 112.

Figure 11:
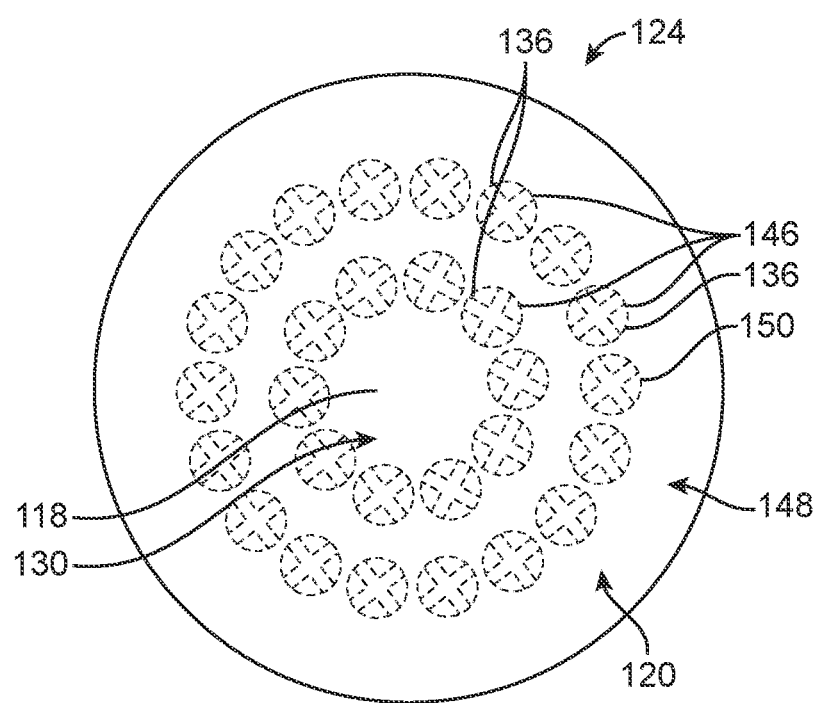
FIG. 11 shows an apparatus to treat refractive error of an eye, in accordance with some embodiments.
Figure 12:
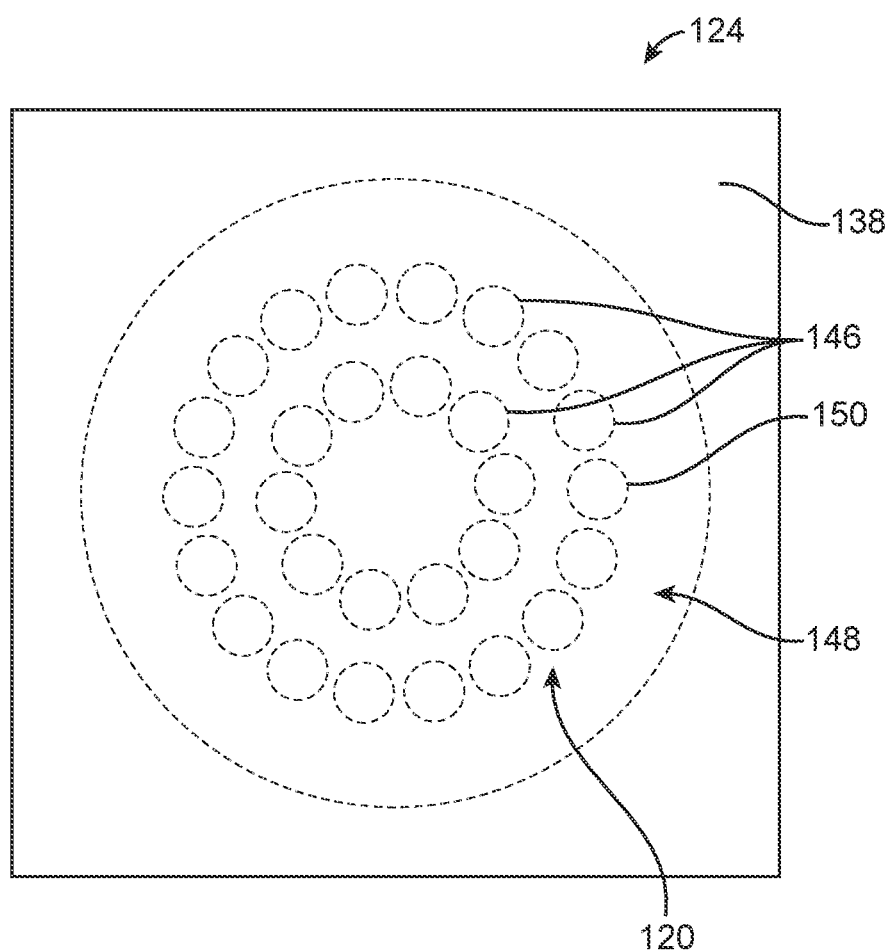
FIG. 12 shows the apparatus of FIG. 11 in use, in accordance with some embodiments.

FIG. 11 depicts a defocus treatment device 124 with a hardware-based defocus structure provided by a plurality of lenslets 146 and stimuli 136 provided by hardware and optionally by software, such as software that modifies the image projected from a display to include stimuli. The defocus treatment device 124 includes a central optical zone 118, and a peripheral defocus optical structure 120. The central optical zone 118 may be plano such that it has substantially planar surfaces or may otherwise be shaped such that it provides little to no change in the angle of the incident light passing through the central optical zone 118. The central optical zone 118 may also include a neutral density filter 130 or mask 150. The defocus treatment device 124 may have a substantially plano anterior surface in non-stimuli areas, for example in areas not including lenslets 146. The neutral density filter 130 filters light passing through the plano regions of the defocus treatment device 124. In some embodiments, the neutral density filter 130 filters light passing through the defocus treatment device 124 in nonstimulated regions of the defocus treatment device 124.

The peripheral area of the defocus treatment device 124 includes a peripheral defocus optical structure 120. The peripheral defocus optical structure 120 may include one or more lenses in the outer region of the device 124. For example, the peripheral defocus optical structure 124 may include an array of lenslets 146 as shown in FIGS. 11 to 15. The plurality of lenslets 146 may be shaped and arranged to provide defocused images to a peripheral portion of the retina while providing clear vision to the fovea and the macula when the user looks ahead.

The lenslets 146 of the peripheral defocus optical structure 120 may be arranged in one or more circular arrays centered about the central optical zone 118 of the defocus treatment device 124. The one or more circular arrays may form an annular shape having an inner diameter and an outer diameter selected such that the peripheral defocus is applied to a portion of the retina of the patient's eye that is eccentric to the fovea. For example, the inner diameter may be selected such that it is at an angle of about 7.5 degrees with respect to an optical axis of the optic 112 and pupil. The outer diameter of the peripheral defocus optical structure 120 may be at an outer boundary angle with respect to the optical axis of the patient's eye and the pupil, for example at 17.5 degrees. Such an arrangement results in the peripheral defocus optical structure 120 being located in a peripheral field of view of the user with a corresponding defocus of the projected light in a peripheral region of the user's retina eccentric to the fovea.

In some embodiments, the location of the lenslets 146 and the unfiltered areas of the defocus treatment device 124 may be positioned with respect to each other such that the light passing through the unfiltered areas of the device 124 also pass through the lenslets 146 such that the unfiltered light is defocused with respect to the patient's retina. In some embodiments, the The defocus treatment device may be used in combination with localized stimuli in the peripheral zone to treat refractive errors of the eye. The localized stimuli may be part of a projected image, for example from a display, or may be provided by structure within or a part of the defocus treatment device.

Stimuli 136, shown in FIGS. 7 and 11, include a lighter area within a darker area as described herein. The stimuli 136 includes a circular area having an unfiltered cross shape inscribed within. The cross shape may include two unfiltered lines intersecting perpendicular to each other, for example, at their midpoints and at the center of the circle. The stimuli may also include wedge shaped neutral density filters 130 or masks 150. Each wedge shaped neutral density filter or mask 150 may fill a quadrant of the circular stimuli formed by the cross-shaped unfiltered areas. In some embodiments, the stimuli may filter light to the same, greater, or lesser extent as the neutral density filter 130 on the non-stimuli areas of the defocus treatment device 124. For example, the stimuli 136 may further reduce light transmission as compared to the unfiltered areas of the stimuli by at least a factor of 5, preferably at least a factor of 10, 20, or 30. In some embodiments, the light transition difference provided by the neutral density filter as compared to non-filtered areas of the defocus treatment device 124 may be a factor of about 5, 10, 20, or 30. In some embodiments the illumination difference may be between a factor of 5 and 30, more preferably between a factor of 10 and 20. In some embodiments, the stimuli 136 may not include a neutral density filter.

In some embodiments, the shaped mask 150 may provide the stimuli. For example, the stimuli of the mask 150 may include images configured in many ways and may include an image structure corresponding to information or content associated with spatial frequencies. In some embodiments, the one or more images projected in the stimuli comprises a spatial frequency within a range from 0.1 cycle per degree to 180 cycles per degree, and optionally a contrast within a range 99.9% to 2.5%, for example. In some embodiments, the one or more images projected in the stimuli comprises a spatial frequency within a range from 1 cycle per degree to 180 cycles per degree, and a contrast within a range 99.9% to 2.5%, for example. In some embodiments, the projected image comprises image structure content configured to provide a range of spatial frequencies, for example within a range from 2 cycles per degree to about 60 cycles per degree. In some embodiments, the image is projected onto the retina with a modulus of an optical transfer function that is equal to or better than 0.3 at a spatial frequency of 50 lp/mm or greater. In some embodiments, the image projected onto the retina comprises spatial frequencies of at least 1 line pair per mm ("lp/mm") on the retina, or greater.

Referring again to FIGS. 3A and 3B, the display 110 may provide video or other image content for projection through the defocus treatment device 124 and into the eye of a user. As discussed above, the defocus treatment device 124 may be placed on anterior to the optic 112, such as a lens of a virtual reality headset or eyeglasses or other devices worn by user. In the embodiments shown in FIG. 12 the video content or other imagery provided by the display 110 may be modified to provide stimuli 136. The stimuli 136 may be provided in the form of increased luminosity or brightness at locations eccentric to the center of the image on the display.

In some embodiments, the stimuli and associated lenslets are sized such that they are about 0.5 to 5 degrees in apparent diameter in the field of view of a user, more preferably about 2 to 3 degrees, and most preferably about 2.3 degrees. In the embodiment shown in FIG. 12 the video content or other imagery provided by light from the display 110 may be modified by the defocus treatment device 124 to provide the stimuli. The hardware stimuli can be provided with crosses, either alternatively to stimuli on the display or in combination with video stimuli on the display.

In the defocus treatment device 124, the video content provided by the display 110 is projected through the lenslets 146 and the stimuli 136 of the mask 150 in the peripheral defocus optical structure 120 and accordingly both the image of the video content and the stimuli 136 are defocused by the peripheral defocus optical structure 120. In some embodiments, the display may include bright locations that align with the stimuli 136 and the lenslets 146 of the peripheral defocus optical structure 120 to provide additional brightness and contrast to the stimuli as compared to the other regions of the defocus treatment device 124.

Figure 13:
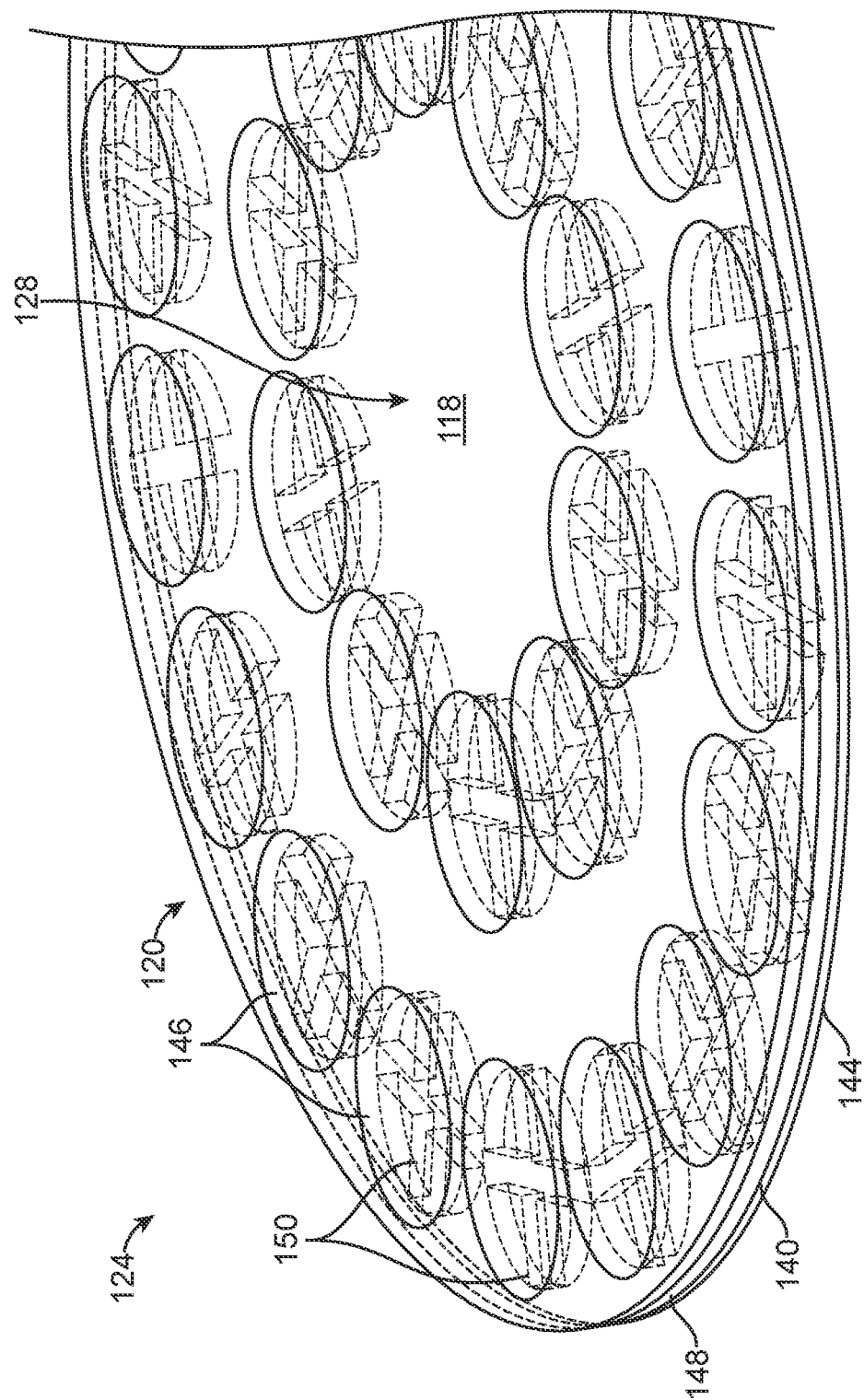
FIG. 13 shows a perspective view of the apparatus of FIG. 11, in accordance with some embodiments.
Figure 14:
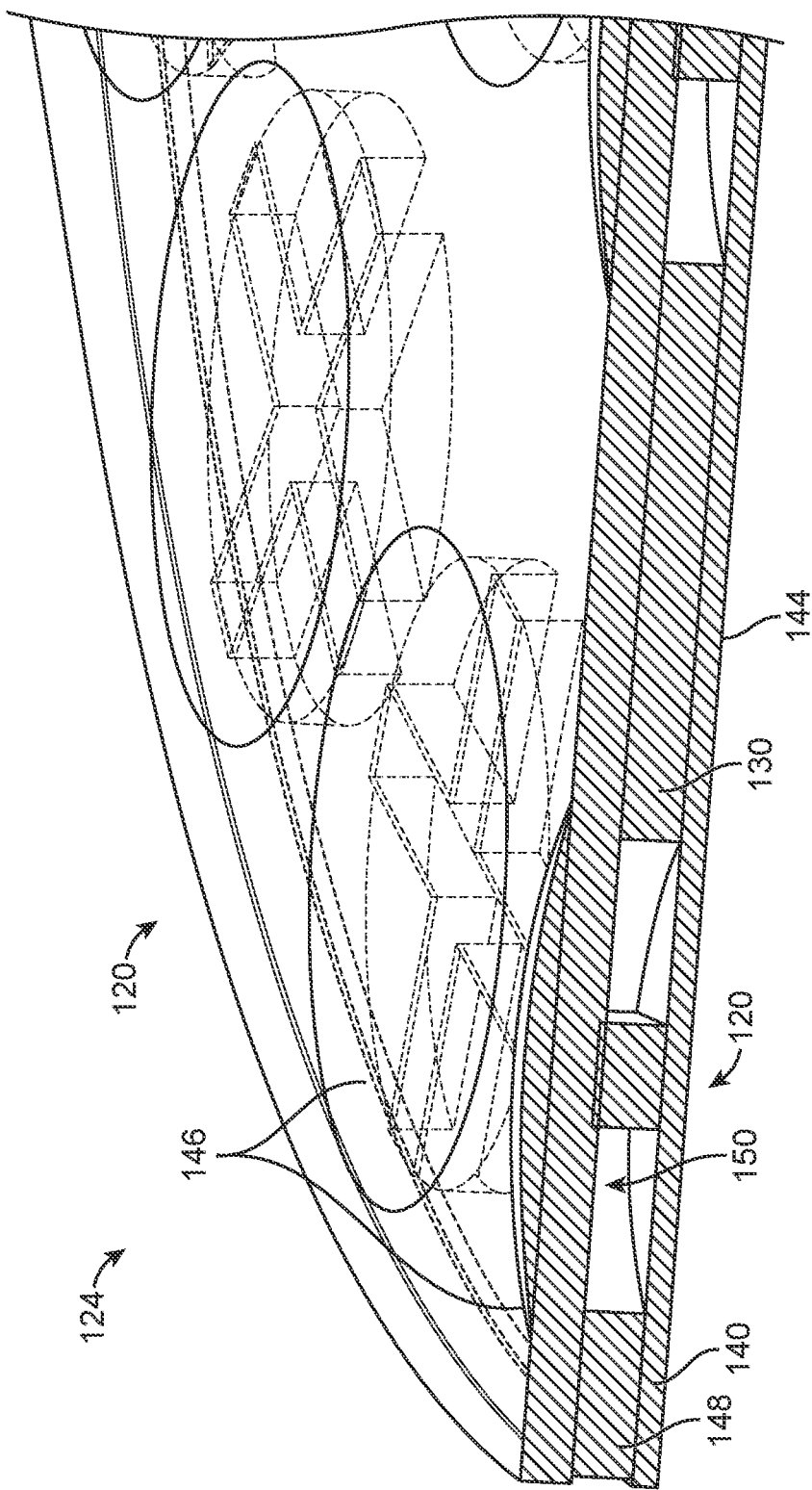
FIG. 14 shows a cross-sectional perspective view of the apparatus of FIG. 11, in accordance with some embodiments.

FIGS. 13 and 14 show a perspective and cross-section of defocus treatment device 124, respectively, including the central optical zone 118 comprising the plano center area 128 and the peripheral defocus optical structure 120 and its associated lenslets 146 and masks 150. The peripheral defocus optical structure 120 may include a plurality of lenslets 146 each having desired optical power to provide defocus with the lenslets. The lenslets for may have other shapes or structures. For example, lenslets may be formed from a diffractive optical structure, echelettes, GRIN lenses, or Fresnel lenses having a shape or structure to create the desired diopter. In some embodiments, the lenslets may be electrically tunable lenses that allow for dynamic variation in the defocus provided by the lenslets 146. For example, in some embodiments the lenslets may provide no defocus during certain periods while providing a defocus of between 2 and 6 D during other periods.

The defocus treatment device 124 may include a neutral density filter 130 or mask layer 148. The mask layer 148 may include a neutral density filter 130 in the areas of the lens that are desired to be darker and have lower illumination. The neutral density filter may be located on a posterior surface of the defocus treatment device 124 opposite an anterior surface on which the peripheral defocus optical structure 120, such as the lenslets 146, is located. In some embodiments, the neutral density filter 130 may extend from the plano center 128 and plano regions to the peripheral defocus optical structure 120 such that a portion of the light passing through the plano regions of the peripheral defocus optical structure 120 is filtered by the neutral density mass 130. In some embodiments, the neutral density filter 130 may not cover locations of the defocus treatment device 124 corresponding to the locations of lenslets 146. The peripheral stimuli 136 may be provided, at least in part, by one or more locations on the defocus treatment device 124 not subject to filtering by the neutral density filter 130. Structures may be formed in or through the neutral density filter 130 to allow unfiltered light to pass through. For example, as shown in the cross-section of FIG. 14, the defocus treatment device 124 includes a neutral density filter 130 and stimuli locations with structures formed to allow unfiltered light to pass through. The structures may be of a shape as discussed above such that they form a bright circular area with or without a light cross shape inscribed within.

The mask 150 that includes the stimuli may be an image or structure formed on the clear base 140 or within the wedge-shaped areas in the neutral density filter 130 at the location of corresponding lenslets 146.

Figure 15:
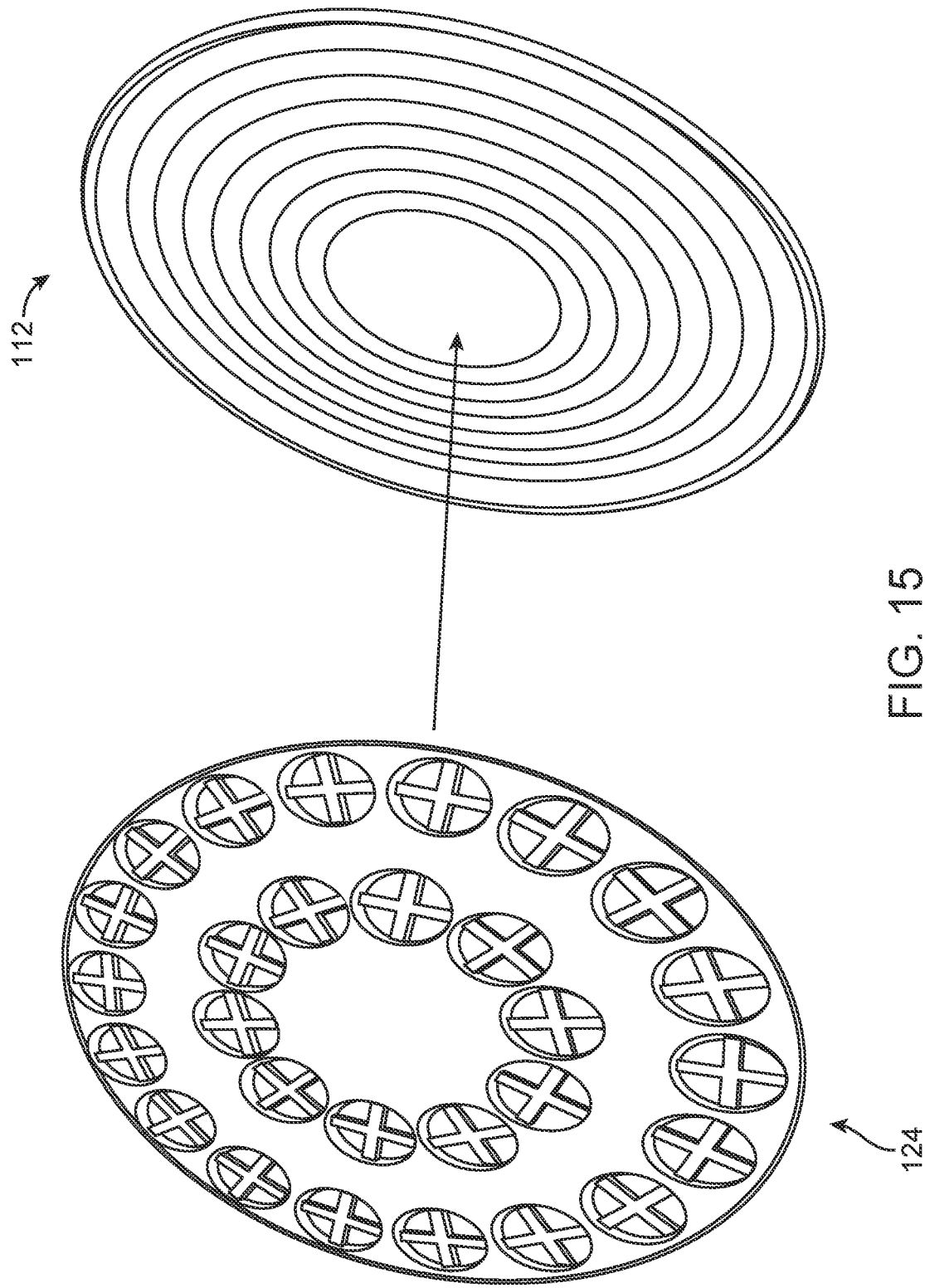
FIG. 15 shows assembly of the apparatus of FIG. 11 onto a lens, in accordance with some embodiments.

With reference to FIGS. 13-15, the defocus treatment device 124 may include a clear base 140 on a posterior side of the defocus treatment device 124 the base 140 may include a lens interface surface 144 for coupling the defocus treatment device 124 to a lens, such as lens 112. In some embodiments, the lens interface surface 144 may include an adhesive to further facilitate coupling the defocus treatment device 124 to a lens or other structure. In some embodiments, the defocus treatment device 124 may be formed directly on or in a lens. In such embodiments, the defocus treatment device 124 may not have a base 140 on an anterior surface or the base 140 may be the optical structure such as the lens 112.

Figure 16:
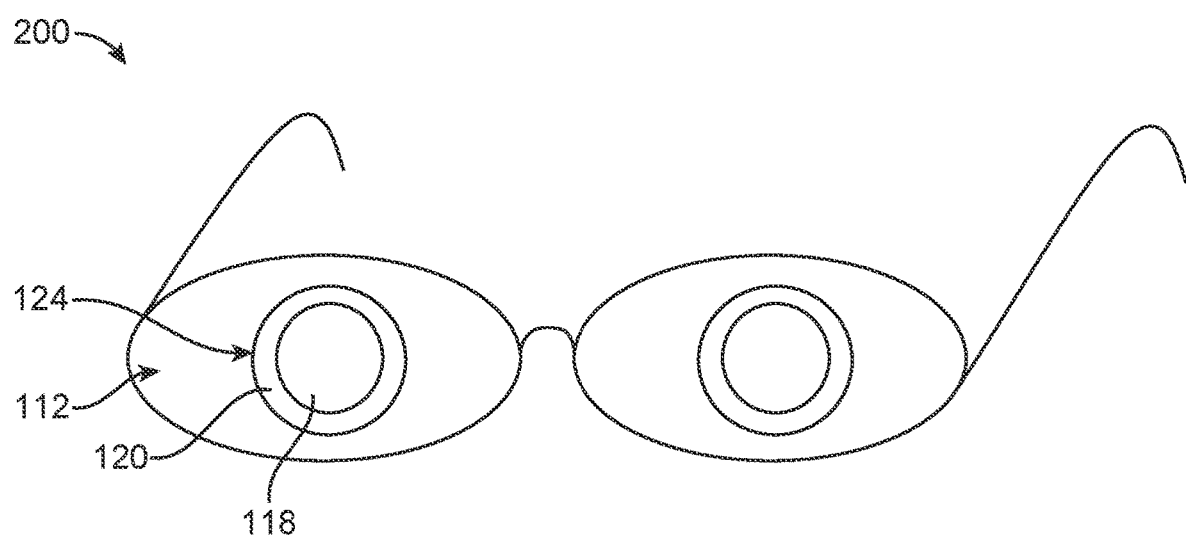
FIG. 16 shows an apparatus to treat refractive error of an eye, in accordance with some embodiments.

FIG. 16 a spectacle 200 that incorporates a defocus treatment device 124 with a hardware-based peripheral defocus optical structure 120 and stimuli provided by hardware, such as a mask, as discussed above with reference to mask 150. The defocus treatment device includes a central optical zone 118, and a peripheral defocus optical structure 120.

The peripheral defocus optical structure 120 may be implemented in many ways, such as any of the structures discussed herein, including a Fresnel lens, lenslets, diffractive optics, or echelettes. The central optical zone 118 and non-stimulated regions of the peripheral defocus optical structure may also include a neutral density filter or mask, as discussed herein. The defocus structure device may be incorporate into the lens 112 of the spectacles or may be a separate structure that is couplable to the lenses 120 or another portion of the spectacles, such as the spectacle frame.

Figure 17:
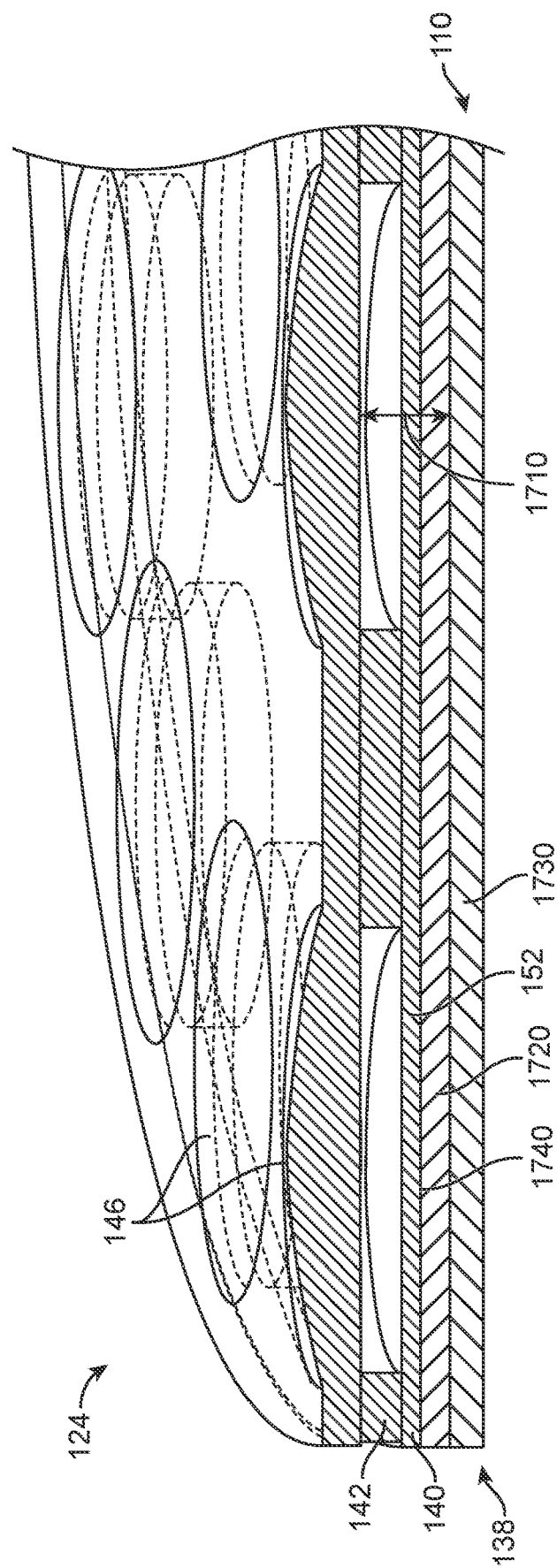
FIG. 17 shows an apparatus comprising a device coupled to a display of a user device to provide retinal stimulation to the user.

FIG. 17 shows a treatment apparatus comprising a device 124 coupled to a display 110 of a device such as a user device to provide retinal stimulation to the user. In some embodiments, the display 110 comprises a protective layer 1720 and a pixel layer 1730. The plurality of lenslets 146 is spaced from the pixel layer 1730 by a distance 1710. The distance 1710 and the optical power of the lenslets can be configured to focus the plurality of stimuli anterior or posterior to the retina with an appropriate amount of defocus.

In some embodiments, the base 140 and the layer 142 each comprises a thickness dimensioned to place the plurality of lenslets 146 at the distance 1710 from the pixel layer 1730. In some embodiments, the defocus treatment device 124 comprises the clear base 140 to couple to the display with the adhesive. The layer 142 may comprise a filter. Alternatively, the layer 142 may comprise a substantially clear layer and the display configured to provide a dark background around the stimuli, for example. In some embodiments, the layer 142 comprises a thickness to place the lenslet array at an appropriate distance 1710 from the pixel layer 1730. Alternatively or in combination, the clear base 140 comprises a thickness to place the lenslet array at the appropriate distance 1710. Although base 140 and layer 142 are shown, in some embodiments, the lenslet array comprises a thickness dimensioned to position the lenslets 146 at the distance 1710 from the pixels 1730 without the base 140 and layer 142. For example, adhesive layer 1740 can couple the lenses of the lenslet array 146 directly to the protective layer 1720 of the display 138 with the lenslets positioned at distance 1710 from the pixel layer 1730.

In some embodiments, the device 124 is coupled to the display with an adhesive layer 1740. Alternatively, the device 124 can be placed in a support such as a holder to place the lenslet array at distance 1710 from the display. In some embodiments, the device 124 is provided to the user with a peelable cover on the adhesive layer for the user to peel the cover and place the device 124 on the display. Although reference is made to layer 1740 comprising an adhesive layer, in some embodiments the layer 1740 comprises a weak adhesive that allows the user to remove the device 124 from the display.

In some embodiments, the lenslets comprise an optical power and the distance 1710 is dimensioned to provide appropriate magnification to the stimulus, so as to provide a suitable distance across each of the plurality of stimuli.

In some embodiments, a processor comprises instructions to provide the plurality of stimuli 136 on the display with appropriate sizes and locations to provide retinal stimulation as described herein. A person of ordinary skill in the art of optics can determine the focal lengths of the lenslets 146 and the distance 1710 between the lenslets and the pixel layer to provide appropriate angular sizing of the stimuli 136 on the display as described herein, for example with reference to FIG. 3B.

In some embodiments, each of the plurality of lenslets is separated from an adjacent lenslet by a gap to decrease optical interference among stimuli, such that each stimulus can be provided to a region of the retina substantially without light from neighboring stimuli. For example, the plurality of stimuli on the display can be separated from each other similarly to the spacing of the lenses of the lenslet array. The display may comprise a substantially dark background with gaps between the stimuli as shown in FIG. 3B. Alternatively, the layer 142 may comprise an optically non-transmissive material that defines apertures or windows of transmissive material corresponding to locations of the lenses, so as to decrease optical interference.

Figure 18:
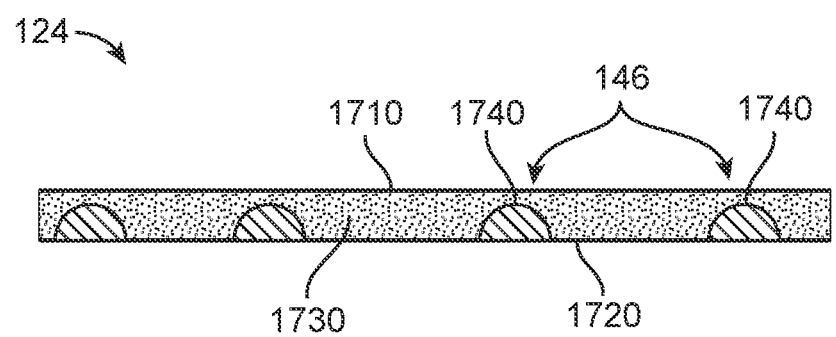
FIG. 18 shows a plurality of lenslets with a liquid crystal material between electrodes.

FIG. 18 shows a plurality of lenslets with a liquid crystal material between electrodes. In some embodiments, the peripheral defocus structure comprises the plurality of lenslets of a lenslet array 146, the electrodes and the liquid crystal ("LC") material in order to activate and deactivate the optical power of the lenslets. In the active configuration, the lenslets comprise optical power to generate the plurality of stimuli. In the inactivate configuration, the optical power of the lenslets is decreased, and appear substantially transparent to the user, so that the user can view the display normally, e.g. through the substantially inactive lenslets.

In some embodiments, the peripheral defocus structure comprises a first electrode 1710 and a second electrode 1720, which are spaced apart with the liquid crystal material 1730 and the lenslets 1740 between the plurality of substantially transparent electrodes. The liquid crystal material and the plurality of lenslets are positioned between the plurality of electrodes to activate and deactivate optical power of the plurality of lenslets.

In some embodiments, the plurality of lenslets between the electrodes can be optically coupled to a display, and the processor of the mobile device is operatively coupled to the display. The processor comprises instructions to provide the plurality of stimuli on the display at a plurality of locations to form the images at a plurality of locations anterior or posterior to the retina. In some embodiments, each of the plurality of stimuli on the display is aligned with a corresponding lenslet to form an image at a location anterior or posterior to a peripheral portion of the retina.

The electrodes, liquid crystal ("LC") material and lenslets can be configured in many ways. In some embodiments, the lenslets comprise one or more of diffractive optics, refractive optics, holographic optics, or echelettes. In some embodiments a potential difference (Voltage) is delivered by a transparent electrode, e.g., Indium Tin Oxide (ITO). The electrode may comprise a thickness within a range from 20 nm to 200 nm. The metal may be deposited on an aligned layer of a substrate, such as an SiO2 layer, that has a thickness within a range from 5 nm to 30 nm. In some embodiments, alignment of the SiO2 layer is achieved by oblique deposition. In some embodiments, the alignment of the SiO2 layer drives alignment of the LC molecules at a lower voltage.

While the coating thickness can be configured in many ways, in some embodiments the thickness is determined with optimization. For example, simulations can be performed to optimize the transmission with ITO-SiO2 coatings. For ITO-SiO2 layers on glass substrate, work in relation to the present disclosure suggests that a thicknesses of 20 nm and 230 nm, respectively, can provide maximum transmission for light at 550 nm at normal incidence. While the transmission can be any suitable amount, e.g. 80% or more, the calculated transmission can be approximately 93.35% at normal incidence for an air/ITO interface, for example. Although reference is made to SiO2 (glass) as a substrate material having an index of refraction of 1.67, the substrate material may comprise any suitable material, such as glass or plastic, for example.

In some embodiments, the liquid crystal material comprises a substantially transparent material with a glass transition temperature below −10 degrees C. and a melting point above 100 degrees C. The liquid crystal material may comprise one or more of a nematic phase, a cholesteric phase or smectic phase. The liquid crystal material may comprise a cholesteric liquid crystal with a dichroic dye. The dichroic dye may have an orientation dependent absorption of light or it may have an orientation dependent average refractive index. Both such properties of dichroic dyes may be used in construction of the electroactive element disclosed herein.

In some embodiments, the liquid crystal material comprises a substantially transparent material with a glass transition temperature below −10 degrees C. and a melting point above 100 degrees C. The liquid crystal material may comprise one or more of a nematic phase, a cholesteric phase or smectic phase. The liquid crystal material may comprise a cholesteric liquid crystal with a dichroic dye. The dichroic dye may have an orientation dependent absorption of light or it may have an orientation dependent average refractive index. Both such properties of dichroic dyes may be used in construction of the electroactive element disclosed herein.

The electroactive component can be configured in many ways. For example, the electroactive component may comprise an assembly configured for placement on the lens at a suitable time during manufacture of the lens. For example, the component may comprise a stand-alone component configured for placement on the lens, either before or after the curved refractive surface has been ground on the lens. The circuitry can be coupled to the electroactive component with suitable connectors and mounted on the support such as an eyeglass frame at a suitable location as described herein.

Table 1 shows liquid crystal formulations commercially available from Merck and their material properties such as refractive indices.

TABLE 1

| LC | $n_e$ | $n_o$ | Birefringence | $n_{avg}$ | $T_C$, °C. | diel. anisotropy | Viscosity, mPa·s |
|---|---|---|---|---|---|---|---|
| MDA-98-1602/PO | 1.7779 | 1.5113 | 0.2666 | 1.6446 | 109 | 11.9 | 203 |
| MLC-2134 | 1.7691 | 1.5106 | 0.2585 | 1.63985 | 112 | — | — |
| MLC-2132 | 1.7657 | 1.5094 | 0.2563 | 1.63755 | 114 | 10.7 | |
| MLC-6080 | 1.71 | 1.5076 | 0.2024 | 1.6088 | 95 | 7.2 | 157 |
| MLC-2136 | 1.7162 | 1.5038 | 0.2124 | 1.61 | 92 | 7.1 | 134 |
| BL 006 | 1.816 | 1.53 | 0.286 | 1.673 | 113 | 17.3 | 71 |
| DIC/PHC | 1.765 | 1.514 | 0.251 | 1.6395 | 99.4 | 16.2 | 43.1 |
| E7 | 1.7394 | 1.5224 | 0.217 | 1.6309 | 61 | 13.2 | — |
| E44 | 1.7859 | 1.52778 | 0.25812 | 1.65684 | — | — | — |
| MDA-05-2986 | 1.781 | 1.5125 | 0.2685 | 1.64675 | — | — | — |

Although reference is made to specific liquid crystal materials, one of ordinary skill in the art will recognize that many adaptations and variations can be made.

A person of ordinary skill in the art can identify lenslet materials suitable for use with the LC material provide appropriate switching of the optical power of the lenslet array. While many materials can be used, examples of lenslet materials include one or more of ion doped glasses, polyacrylates, polymethacrylates, polyaromatics, polysulfones, polyimides, polyamides, polyethers, polyether ketones, or polycyclic olefins.

In some embodiments, the liquid crystal material is switchable from a first refractive index in the first configuration to substantially refract light with the lenslet array to a second refractive index in a second configuration to substantially transparently transmit light without substantial optical power from the lenslet array. The second refractive index is closer to a refractive index of the lenslet array to decrease optical power from the lenslet array in the second configuration.

In some embodiments, the first refractive index differs from the refractive index of the lenslet array by at least 0.05 to provide substantial optical power to the lenslet array and the second refractive index differs from the refractive index of the lenslet array by no more than 0.02 to provide substantially decrease optical power and substantially transparently transmit light through the lenslet array, such that the presence of the lenslet array is not perceptible to the user.

In some embodiments, the liquid crystal material is configured to provide a change in refractive index within a range from 0.10 to 0.25.

Figure 19:
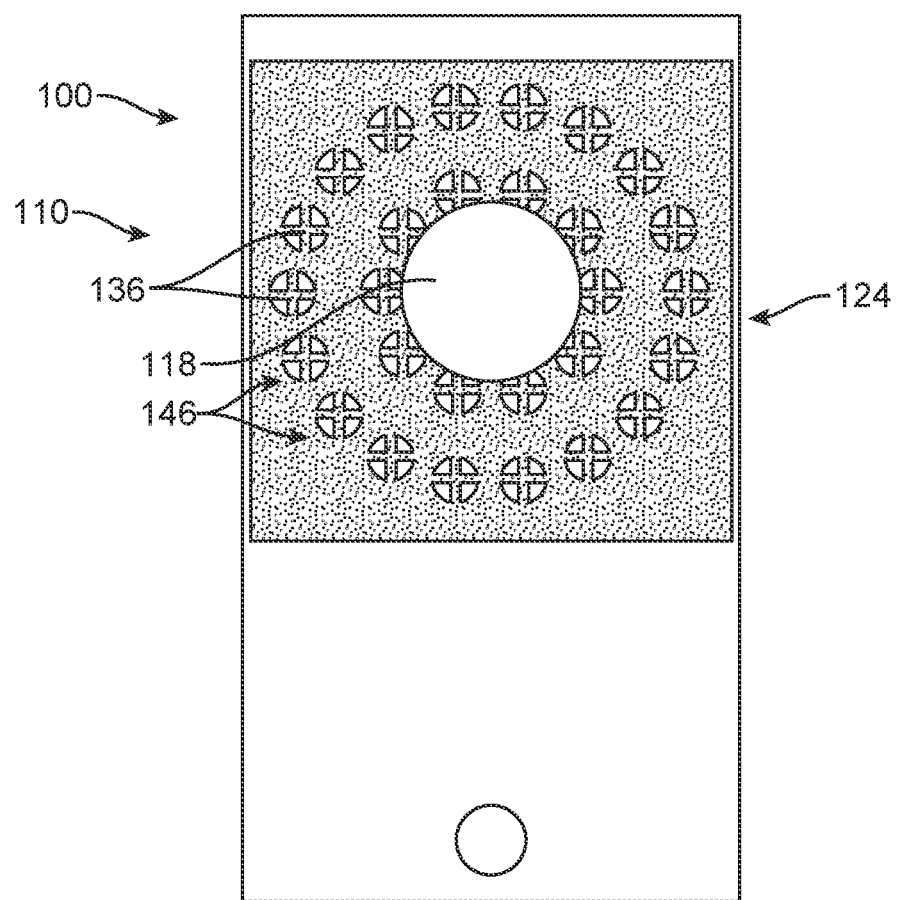
FIG. 19 shows a treatment apparatus comprising a display coupled to a lenslet array, in accordance with some embodiments.

FIG. 19 shows a treatment apparatus 100 comprising a display 110 coupled to a lenslet array 146 of a treatment device 124 as described herein. The apparatus 100 can be configured in many ways, and may comprise a user device comprising one or more of an ophthalmic device, a TV screen, a computer screen, a VR display, an AR display, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. In some embodiments, the treatment device comprises a user device, such as a smart phone or tablet, for example. The display of the user device can be configured to provide a plurality of stimuli 136 as described herein. In some embodiments, the user device comprises lenslet array 146 placed over the plurality of stimuli, so as to provide an image of the stimuli anterior or posterior to the retina. In some embodiments, each lenslet of the lenslet array is aligned with one of the plurality of stimuli. The user device may comprise a zone 118 with a clear viewing area as described herein, for example without the lenslet array extending into the clear viewing area. The clear viewing area can be configured for the user to view images, such as videos and allow the user to use the device in a substantially normal manner, for example so as to use a web browser, play video games, send and receive texts and emails, etc. The lenslet array can be positioned at a distance from the pixels so as to provide an appropriate amount of defocus as described herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

A generally accepted unit of optical power is the Diopter ("D"), which is related to the inverse of the focal length of a lens in meters. In some embodiments, a defocus optical structure comprises optical power to alter the focus of light with respect to the retina. A defocus optical structure may comprise positive optical power to form an image of a stimulus anterior to the retina, or negative optical power to form the image of the stimulus posterior to the retina. In some embodiments, myopic defocus corresponds to positive optical power, which can be expressed with positive values in Diopters, and that hyperopic defocus corresponds to negative optical power, which can be expressed in negative values in Diopters.

The present disclosure includes the following numbered clauses.

Clause 1. An apparatus to treat refractive error of an eye, the apparatus comprising: an optic comprising an optical zone; and a peripheral defocus optical structure to form images of a plurality of stimuli anterior or posterior to a peripheral portion of a retina of the eye, the peripheral defocus optical structure located outside the optical zone.

Clause 2. The apparatus of clause 1, wherein the peripheral defocus optical structure comprises optical power to focus light to a different depth of the eye than the optical zone.

Clause 3. The apparatus of clause 1, wherein the optic comprises one or more of a lens, an optically transparent substrate, a beam splitter, a prism, or an optically transmissive support.

Clause 4. The apparatus of clause 1, wherein peripheral defocus optical structure comprises a Fresnel lens.

Clause 5. The apparatus of clause 1, wherein peripheral defocus optical structure comprises a plurality of lenslets.

Clause 6. The apparatus of clause 5, wherein a plurality of lenslets is arranged in one or more circular arrays about the optical zone.

Clause 7. The apparatus of clause 1, wherein peripheral defocus optical structure comprises one or more of a diffractive optical structure or echelettes.

Clause 8. The apparatus of clause 1, further comprising a filter within the optical zone to decrease light transmission therethrough.

Clause 9. The apparatus of clause 8, wherein the filter is configured to decrease an intensity of a central image formed on a fovea of the eye and provide an increased intensity of the plurality of stimuli in relation to the intensity of the central image.

Clause 10. The apparatus of clause 8, wherein the filter extends into the peripheral defocus optical structure.

Clause 11. The apparatus of clause 8, wherein the filter comprises a neutral density filter.

Clause 12. The apparatus of clause 8, wherein the filter reduces transmission of visible light by a factor of between 5 and 30.

Clause 13. The apparatus of clause 8, wherein the filter reduces transmission of visible light by an amount within a range from 5 percent to 99 percent.

Clause 14. The apparatus of clause 1, further comprising a display that is configured to provide light through the optical zone to form a central image on a macula and through the peripheral defocus optical structure to provide the plurality of stimuli with defocus on the peripheral portion of the retina.

Clause 15. The apparatus as in clause 14, wherein plurality of stimuli is formed with lenslets of the peripheral defocus optical structure.

Clause 16. The apparatus of clause 1, wherein the peripheral defocus optical structure further comprises a plurality of stimuli generating structures.

Clause 17. The apparatus of clause 16, further comprising a filter aligned with one or more apertures of the peripheral defocus optical structure.

Clause 18. The apparatus of clause 17, wherein the plurality of stimuli generating structures are within the aperture.

Clause 19. The apparatus of clause 18, wherein each of the plurality of stimuli generating structures comprise a mask.

Clause 20. The apparatus of clause 1, wherein the each of the plurality of stimuli comprises spatial frequencies.

Clause 21. The apparatus of clause 20, wherein the spatial frequencies comprise frequencies within a range from 0.1 cycles per degree to 180 cycles per degree and optionally within a range from 1 cycle per degree to 180 cycles per degree.

Clause 22. The apparatus of clause 20, wherein the spatial frequencies comprise frequencies of at least 1 line pair per mm (lp/mm) on the retina and optionally at least 50 lp/mm on the retina.

Clause 23. The apparatus of clause 1, wherein the plurality of stimuli comprise contrast within a range 99.9% to 2.5%.

Clause 24. The apparatus of clause 1, wherein the peripheral defocus optical structure comprises an optical power within a range from −2 D to −6 D or within a range from +2D to +6D.

Clause 25. The apparatus of clause 1, wherein the peripheral defocus optical structure comprises an optical power within a range from −3 D to −5 D or within a range from +3 D to +5 D.

Clause 26. The apparatus of clause 1, further comprising a base, wherein the peripheral defocus optical structure is coupled to the base.

Clause 27. The apparatus of clause 26, further comprising adhesive on a surface of the base.

Clause 28. The apparatus of clause 27, wherein the optic comprises a spectacle lens and a filter and peripheral defocus optical structure are coupled to the lens.

Clause 29. The apparatus of clause 1, wherein the optic comprises an adhesive.

Clause 30. The apparatus of clause 1, wherein the optic comprises a plurality of layers.

Clause 31. The apparatus of clause 1, further comprising: a display; and a processor operatively coupled to the display, wherein the processor comprises instructions to provide the plurality of stimuli on the display at a plurality of locations to form the images at a plurality of locations anterior or posterior to the retina.

Clause 32. The apparatus of clause 31, wherein the peripheral defocus structure comprises a plurality of lenslets, and wherein the each of the plurality of stimuli on the display is aligned with a corresponding lenslet to form an image at a location anterior or posterior to a peripheral portion of the retina.

Clause 33. The apparatus of clause 32, further comprising: a plurality of substantially transparent electrodes; and a liquid crystal material between the plurality of substantially transparent electrodes; wherein the liquid crystal material and the plurality of lenslets are positioned between the plurality of electrodes to activate and deactivate optical power of the plurality of lenslets.

Clause 34. The apparatus of clause 33, wherein the plurality of lenslets is substantially transparent in a deactivated configuration and wherein the plurality of lenslets is configured to provide the plurality of stimuli in a deactivated configuration.

Clause 35. The apparatus of clause 33, wherein the plurality of electrodes is configured to change an index of refraction of the liquid crystal material in response to a voltage between the electrodes.

Clause 36. The apparatus of clause 33, wherein the processor is operatively coupled to the plurality of electrodes to activate the plurality of lenslets to provide the plurality of stimuli.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus to treat refractive error of an eye, the apparatus comprising:
    an optic comprising an optical zone; and
    a peripheral defocus optical structure comprising a plurality of lenslets to form images of a plurality of stimuli anterior or posterior to a peripheral portion of a retina of the eye, the peripheral defocus optical structure located outside the optical zone;
    a plurality of substantially transparent electrodes; and
    a liquid crystal material between the plurality of substantially transparent electrodes;
    wherein the liquid crystal material and the plurality of lenslets are positioned between the plurality of substantially transparent electrodes to activate and deactivate optical power of the plurality of lenslets.

2. The apparatus of claim 1, wherein the peripheral defocus optical structure comprises an optical power to focus light to a different depth of the eye than the optical zone.

3. The apparatus of claim 1, wherein the optic comprises one or more of a lens, an optically transparent substrate, a beam splitter, a prism, or an optically transmissive support.

4. The apparatus of claim 1, wherein the peripheral defocus optical structure comprises a Fresnel lens.

5. The apparatus of claim 1, wherein the peripheral defocus optical structure comprises a plurality of lenslets.

6. The apparatus of claim 5, wherein the plurality of lenslets is arranged in one or more circular arrays about the optical zone.

7. The apparatus of claim 1, wherein the peripheral defocus optical structure comprises one or more of a diffractive optical structure or echelettes.

8. The apparatus of claim 1, further comprising a filter within the optical zone to decrease light transmission therethrough.

9. The apparatus of claim 8, wherein the filter is configured to decrease an intensity of a central image formed on a fovea of the eye and provide an increased intensity of the plurality of stimuli in relation to the intensity of the central image.

10. The apparatus of claim 8, wherein the filter extends into the peripheral defocus optical structure.

11. The apparatus of claim 8, wherein the filter comprises a neutral density filter.

12. The apparatus of claim 8, wherein the filter reduces transmission of visible light by a factor of between 5 and 30.

13. The apparatus of claim 8, wherein the filter reduces transmission of visible light by an amount within a range from 5 percent to 99 percent.

14. The apparatus of claim 1, further comprising:
    a display; and
    a processor operatively coupled to the display, wherein the processor comprises instructions to provide the plurality of stimuli on the display at a plurality of locations to form the images at a plurality of locations anterior or posterior to the retina.

15. The apparatus of claim 14, wherein each of the plurality of stimuli on the display is aligned with a corresponding lenslet to form an image at a location anterior or posterior to a peripheral portion of the retina.

16. The apparatus of claim 1, wherein the plurality of lenslets is substantially transparent in a deactivated configuration and wherein the plurality of lenslets is configured to provide the plurality of stimuli in a deactivated configuration.

17. The apparatus of claim 1, wherein the plurality of substantially transparent electrodes is configured to change an index of refraction of the liquid crystal material in response to a voltage between the plurality of substantially transparent electrodes.

18. The apparatus of claim 1, wherein a processor is operatively coupled to the plurality of substantially transparent electrodes to activate the plurality of lenslets to provide the plurality of stimuli.

* * * * *